US012616439B2

(12) United States Patent
Sun et al.

(10) Patent No.: US 12,616,439 B2
(45) Date of Patent: May 5, 2026

(54) LESION LOCATING METHOD AND LESION LOCATING SYSTEM

(71) Applicant: CHONGQING HAIFU MEDICAL TECHNOLOGY CO., LTD., Chongqing (CN)

(72) Inventors: Minyi Sun, Chongqing (CN); Hongbing Hu, Chongqing (CN); Ying Zou, Chongqing (CN); Bing Fu, Chongqing (CN); Xiaobing Wu, Chongqing (CN); Liang Hu, Chongqing (CN); Cai Zhang, Chongqing (CN); Haoran Huang, Chongqing (CN)

(73) Assignee: CHONGQING HAIFU MEDICAL TECHNOLOGY CO., LTD., Chongqing (CN)

( * ) Notice: Subject to any disclaimer, the term of this patent is extended or adjusted under 35 U.S.C. 154(b) by 175 days.

(21) Appl. No.: 18/031,456

(22) PCT Filed: Aug. 30, 2021

(86) PCT No.: PCT/CN2021/115360
§ 371 (c)(1),
(2) Date: Apr. 12, 2023

(87) PCT Pub. No.: WO2022/134647
PCT Pub. Date: Jun. 30, 2022

(65) Prior Publication Data
US 2023/0371920 A1 Nov. 23, 2023

(30) Foreign Application Priority Data
Dec. 24, 2020 (CN) .......................... 202011551545.3

(51) Int. Cl.
A61B 8/00 (2006.01)
A61B 8/08 (2006.01)

(52) U.S. Cl.
CPC ............ *A61B 8/085* (2013.01); *A61B 8/4416* (2013.01); *A61B 8/463* (2013.01); *A61B 8/5261* (2013.01)

(58) Field of Classification Search
CPC ....... A61B 8/085; A61B 8/4416; A61B 8/463; A61B 8/5261
See application file for complete search history.

(56) References Cited

U.S. PATENT DOCUMENTS 6,300,974 B1 10/2001 Viala et al.
6,500,119 B1 * 12/2002 West .................... A61B 5/4312
600/443
(Continued)

FOREIGN PATENT DOCUMENTS

CN 101569541 A 11/2009
CN 202982047 U 6/2013
(Continued)

OTHER PUBLICATIONS

First Examination Report for Related Application No. AU2021406651 dated Apr. 3, 2024.
(Continued)

*Primary Examiner* — Khai M Nguyen
(74) *Attorney, Agent, or Firm* — The Webb Law Firm

(57) ABSTRACT

The lesion locating method includes locating a lesion by locating a mark on a body surface; using a camera in locating to assist an ultrasound probe for locating; forming a reference view according to data acquired in real time by the camera, where the reference view has a preset size, and a virtual mark point corresponding to the mark is formed in the reference view; and determining, according to a position of the virtual mark point in in the reference view and an actual positional relationship of the camera and the ultrasound probe, an actual locating trajectory that enables a center line of the ultrasound probe to coincide with the mark.

(Continued)

The camera is configured to acquire camera data to form the reference view, and then assists the ultrasound probe for locating with the reference view.

20 Claims, 15 Drawing Sheets

(56) References Cited

U.S. PATENT DOCUMENTS

| | | | | |
|---|---|---|---|---|
| 8,165,372 | B2* | 4/2012 | Ishikawa | A61B 8/4254 |
| | | | | 382/128 |
| 2002/0065461 | A1 | 5/2002 | Cosman | |
| 2004/0215072 | A1 | 10/2004 | Zhu | |
| 2005/0031176 | A1 | 2/2005 | Hertel et al. | |
| 2007/0225553 | A1 | 9/2007 | Shahidi | |
| 2009/0275830 | A1 | 11/2009 | Falco et al. | |
| 2012/0101388 | A1 | 4/2012 | Tripathi | |
| 2013/0217947 | A1 | 8/2013 | Fishman | |
| 2018/0046875 | A1 | 2/2018 | Caluser | |
| 2018/0199990 | A1* | 7/2018 | Monir | A61B 18/1492 |
| 2019/0209119 | A1 | 7/2019 | Mauldin, Jr. et al. | |
| 2019/0261947 | A1* | 8/2019 | Themelis | A61B 5/0071 |
| 2020/0069976 | A1 | 3/2020 | Puleo et al. | |
| 2020/0138408 | A1 | 5/2020 | Zheng | |
| 2020/0242971 | A1 | 7/2020 | Wang et al. | |
| 2022/0126121 | A1 | 4/2022 | Puleo et al. | |

FOREIGN PATENT DOCUMENTS

| | | | |
|---|---|---|---|
| CN | 105030275 | A | 11/2015 |
| CN | 103893919 | B * | 2/2017 |
| CN | 106952347 | A | 7/2017 |
| CN | 107638635 | A | 1/2018 |
| CN | 107865671 | A | 4/2018 |
| CN | 109171817 | A | 1/2019 |
| CN | 109223030 | A | 1/2019 |
| CN | 110192894 | A | 9/2019 |
| CN | 112704514 | A | 4/2021 |
| JP | 7375180 | B2 | 11/2023 |
| WO | 2014113530 | A1 | 7/2014 |

OTHER PUBLICATIONS

Office Action for Related Application No. CN 202011551545.3 dated Aug. 27, 2021.

Office Action for Related Application No. EP21908650.1 dated Nov. 17, 2025.

International Search Report for Related Application PCT/CN2021/115360 dated Dec. 6, 2021.

Decision of Patent for Related Patent No. JP 2023-524412 dated Sep. 10, 2024.

Office Action for Related Patent No. JP 2023-524412 dated Mar. 12, 2024.

Office Action for Related Patent No. KR1020237015344 dated Apr. 14, 2025.

Notice of Allowance for Related Patent No. KR1020237015344 dated Dec. 12, 2025.

Office Action for Related Patent No. RU2023109639 dated Aug. 15, 2023.

* cited by examiner

LESION LOCATING METHOD AND LESION LOCATING SYSTEM

CROSS REFERENCE TO RELATED APPLICATIONS

This application is the United States national phase of International Patent Application No. PCT/CN2021/115360 filed Aug. 30, 2021, and claims priority to Chinese Patent Application No. 202011551545.3 filed Dec. 24, 2020, the disclosures of which are hereby incorporated by reference in their entireties.

BACKGROUND OF THE INVENTION

Field of the Invention

The present disclosure belongs to the technical field of ultrasound treatment, and in particular relates to a lesion locating method and a lesion locating system.

Description of Related Art

By focusing ultrasonic waves, the high-intensity focused ultrasound treatment technology can form high-intensity and continuous ultrasonic energy on a lesion, thereby generating a transient high-temperature effect, a cavitation effect, a mechanical effect and a sonochemical effect, breaking cell membranes and nuclear membranes, coagulating protein, and selectively causing coagulative necrosis of lesion tissues to disable proliferation, infiltration and transfer capabilities of the lesion.

In the treatment process with an existing ultrasound treatment device, a B-mode ultrasound probe is usually used for guiding location of a lesion, and the B-mode ultrasound probe needs to be repeatedly moved for many times in the locating process to help a doctor to imagine a surrounding anatomical structure of the lesion, and analyze and find a location of the lesion, which is complicated and consumes a lot of time.

SUMMARY OF THE INVENTION

In view of the above disadvantages of the existing art, an object of the present disclosure is to provide a lesion locating method and a lesion locating system which can solve the problems of complicated process and long time consumption in locating a lesion in the existing art.

To achieve the above and other related objects:

the present disclosure provides a lesion locating method involving locating a lesion by locating a mark on a body surface; using an image acquisition assembly in locating to locate the mark, wherein the image acquisition assembly includes an ultrasound probe, and at least one camera distributed on one side or both sides of a sector-scanning plane of the ultrasound probe and fixed in position relative to the ultrasound probe, and a center line of the camera is parallel to a center line of the ultrasound probe, and the lesion locating method includes:

forming a reference view according to data acquired in real time by the camera, wherein the reference view has a preset size, and a virtual mark point corresponding to the mark is formed in the reference view; and determining, according to a position of the virtual mark point in the reference view and an actual positional relationship of the camera and the ultrasound probe, an actual locating trajectory that enables the center line of the ultrasound probe to coincide with the mark.

Optionally, forming the reference view according to the data acquired in real time by the camera includes:

inputting a pre-locating instruction, according to which the image acquisition assembly is moved to a position above the mark;

judging, when the image acquisition assembly completes the pre-locating instruction, whether a current view acquired and formed by the camera in real time contains a virtual mark point corresponding to the mark;

taking, if the current view contains the virtual mark point corresponding to the mark, the current view as the reference view and a current height distance of the ultrasound probe to the mark as a pre-locating height, and inputting, if the current view does not contain the virtual mark point corresponding to the mark, the pre-locating instruction again, until the reference view is formed.

Optionally, calculating the actual locating trajectory further includes:

limiting, according to the pre-locating height, a motion boundary condition of the image acquisition assembly so that the ultrasound probe is movable within a preset plane, wherein the preset plane is a plane perpendicular to the center line of the ultrasound probe and corresponding to the pre-locating height.

Optionally, forming the reference view includes:

establishing an imaging proportional relation between the current view and an actual acquisition region of the camera, and forming the reference view according to the imaging proportional relation;

setting a preset value of the pre-locating height, and inputting a pre-locating instruction so that the pre-locating height is equal to the preset value and the proportional relation is a fixed value;

or establishing a calculation model of the imaging proportional relation by taking the preset value of the pre-locating height as a variable, and calculating an actual imaging proportional relation after obtaining a value of the pre-locating height;

or setting an installation position of the camera so that part of a side edge contour of the ultrasound probe always exists in the current view acquired by the camera, and calculating, when establishing the imaging proportional relation, the imaging proportional relation from an actual distance from the center line of the camera to the side edge contour and a reference distance in the reference view.

Optionally, when the center line of the camera is located on a midperpendicular plane of the sector-scanning plane of the ultrasound probe and the reference view is formed, the center line of the camera is located at a center of the reference view, the reference view takes a projection of the midperpendicular plane of the ultrasonic sector-scanning plane as a transverse axis and a direction perpendicular to the transverse axis as a longitudinal direction, and calculating the actual locating trajectory includes: calculating an actual transverse displacement and an actual longitudinal displacement, respectively, wherein calculating the actual longitudinal displacement includes:

moving, according to a position of the virtual mark point in the reference view, the virtual mark point to a virtual longitudinal displacement desired to coincide with the transverse axis, and

calculating the actual longitudinal displacement according to the virtual longitudinal displacement and the imaging proportional relation.

Optionally, one camera is provided, and calculating the actual transverse displacement includes: calculating a virtual transverse displacement of the virtual mark point according to the position of the virtual mark point in the reference view, and calculating the actual transverse displacement according to the virtual transverse displacement and the imaging proportional relation, wherein a calculation formula of the virtual transverse displacement satisfies:

$$L_0 = \frac{\arctan\frac{h_1 + h_2}{a} - \frac{\pi - \theta}{2}}{\theta} \times L$$

where $L_0$ is a virtual transverse displacement component, a is a center distance between the ultrasound probe and the camera, $h_1$ is a height distance between the ultrasound probe and the camera, $h_2$ is the pre-locating height, $\theta$ is a viewing angle corresponding to an acquisition region of the camera in the transverse direction, and L is a view width corresponding to the reference view in the transverse direction.

Optionally, two cameras are provided, including a first camera and a second camera, wherein the first camera and the second camera are symmetrically distributed on two sides of the sector-scanning plane of the ultrasound probe, and have a same height difference from the ultrasound probe, the first camera acquires data and forms a first reference view, and the second camera acquires data and forms a second reference view, and calculating the actual transverse displacement includes calculating the actual transverse displacement from a position of the virtual mark point in the first reference view and a position of the virtual mark point in the second reference view, wherein a calculation formula of the actual transverse displacement satisfies:

$$y = \frac{\tan\left(\frac{L_2}{L}\theta\right) - \tan\left(\frac{L_1}{L}\theta\right)}{\tan\left(\frac{L_1}{L}\theta\right) + \tan\left(\frac{L_2}{L}\theta\right)}a$$

where y is an actual transverse displacement component, a is a center distance between the ultrasound probe and each camera, $L_1$ is a transverse distance between the virtual mark point in the first reference view and a view center; and $L_2$ is a transverse distance between the virtual mark point in the second reference view and the view center; images acquired by the first camera and the second camera each have a viewing angle $\theta$ in the transverse direction; and the first reference view and the second reference view each have a preset view width L.

Optionally, two cameras are provided, including a first camera and a second camera, wherein the first camera and the second camera are distributed on two sides of the sector-scanning plane of the ultrasound probe, at least one of the first camera or the second camera has a center line deviating from a midperpendicular plane of the sector-scanning plane of the ultrasound probe, and the first camera and the second camera have a same height difference from the ultrasound probe, the first camera acquires data and forms a first reference view, and the second camera acquires data and forms a second reference view, and calculating the actual locating trajectory includes: calculating a virtual transverse displacement and a virtual longitudinal displacement according to positions of the virtual mark point in the first reference view and the second reference view; and calculating an actual transverse displacement and an actual longitudinal displacement according to the virtual transverse displacement, the virtual longitudinal displacement and the imaging proportional relation; wherein in calculation of the virtual transverse displacement and the virtual longitudinal displacement, a virtual projection point of the center line of the ultrasound probe is taken as an origin, a virtual sector-scanning projection line of the sector-scanning plane of the ultrasound probe is taken as a Y axis, and a virtual midperpendicular projection line of the midperpendicular plane of the sector-scanning plane of the ultrasound probe is taken as an X axis to establish a coordinate system, and according to the positions of the virtual mark point in the first reference view and the second reference view, a coordinate calculation formula set of the virtual mark point is established:

$$y_1 = (\tan\theta_1)x_1 + b_1 - a_1\tan\theta_1;$$

$$y_1 = (\tan\theta_2)x_1 + b_2 - a_2\tan\theta_2;$$

where coordinates of the virtual mark point 41 are $(x_1, y_1)$, $\theta_1$ is an angle between the virtual mark point 41 and the sector-scanning plane of the ultrasound probe (corresponding to the X axis) in the first reference view 4a, a coordinate position of the first camera 21 is $(a_1, b_1)$, a coordinate position of the second camera 22 is $(a_2, b_2)$, and $\theta_2$ is an angle between the virtual mark point 41 and the sector-scanning plane of the ultrasound probe (corresponding to the X axis) in the second reference view 4b.

Optionally, a reference scale with fixed position and shape is set corresponding to the reference view, wherein the reference scale has corresponding scale values which are converted into and displayed as size values corresponding to the actual acquisition region of the camera according to an imaging proportion.

Optionally, cameras are divided into at least two camera groups, each of which includes one or two cameras, an actual locating trajectory to be verified is formed according to a reference view acquired and formed by a camera group, and a final actual locating trajectory is obtained according to at least two actual locating trajectories to be verified, wherein:

at least two cameras are provided, including a first camera and a second camera, wherein the first camera and the second camera are symmetrically distributed on two sides of the sector-scanning plane of the ultrasound probe, and each have a center line on a midperpendicular plane of the sector-scanning plane of the ultrasound probe and a same height difference from the ultrasound probe, and while locating a lesion, a first actual locating trajectory is calculated from a corresponding reference view formed by the first camera or the second camera, a second actual locating trajectory is calculated from corresponding reference views formed by the first camera and the second camera, and a final actual locating trajectory is determined from the first actual locating trajectory and the second actual locating trajectory;

or at least two cameras are provided, including a first camera and a second camera, wherein the first camera and the second camera are distributed on two sides of the sector-scanning plane of the ultrasound probe, a center line of the first camera is located on the midperpendicular plane of the sector-scanning plane of the ultrasound probe, while a center line of the second camera deviates from the midperpendicular plane of the sector-scanning plane of the ultrasound probe, the first camera and the second camera have a same height difference from the ultrasound probe, and while locating a lesion, a first actual locating trajectory is calculated from a corresponding reference view formed by the first camera, a second actual locating trajectory is calculated from corresponding reference views formed by the two cameras, and a final actual locating trajectory is determined from the first actual locating trajectory and the second actual locating trajectory;

or at least three cameras are provided, including a first camera, a second camera and a third camera, wherein the first camera and the third camera are distributed on one side of the sector-scanning plane of the ultrasound probe, the second camera is distributed on the other side of the sector-scanning plane of the ultrasound probe, a center line of the third camera is located on the midperpendicular plane of the sector-scanning plane of the ultrasound probe, while center lines of the first camera and the second camera deviate from the midperpendicular plane of the sector-scanning plane of the ultrasound probe, the first camera, the second camera and the third camera have a same height difference from the ultrasound probe, and while locating a lesion, a first actual locating trajectory is calculated from a corresponding reference view formed by the third camera, a second actual locating trajectory is calculated from corresponding reference views formed by the first camera and the second camera, and a final actual locating trajectory is determined from the first actual locating trajectory and the second actual locating trajectory;

or at least four cameras are provided, including a first camera, a second camera, a third camera and a fourth camera, wherein the first camera and the second camera are symmetrically distributed on two sides of the sector-scanning plane of the ultrasound probe, and each have a center line on the midperpendicular plane of the sector-scanning plane of the ultrasound probe, while the third camera and the fourth camera are distributed on two sides of the sector-scanning plane of the ultrasound probe, and each have a center line deviating from the midperpendicular plane of the sector-scanning plane of the ultrasound probe, a first actual locating trajectory is calculated from corresponding reference views formed by the first camera and the second camera, a second actual locating trajectory is calculated from corresponding reference views formed by the third camera and the fourth camera, and a final actual locating trajectory is determined from the first actual locating trajectory and the second actual locating trajectory;

or at least four cameras are provided, including a first camera, a second camera, a third camera and a fourth camera, wherein the first camera and the second camera are symmetrically distributed on two sides of the sector-scanning plane of the ultrasound probe, and each have a center line on the midperpendicular plane of the sector-scanning plane of the ultrasound probe, while the third camera and the fourth camera are distributed on two sides of the sector-scanning plane of the ultrasound probe, and each have a center line deviating from the midperpendicular plane of the sector-scanning plane of the ultrasound probe, a first actual locating trajectory is calculated from corresponding reference views formed by the first camera and the second camera, a second actual locating trajectory is calculated from corresponding reference views formed by the third camera and the fourth camera, and a third actual locating trajectory is calculated from a corresponding reference view formed by the first camera or the second camera, and a final actual locating trajectory is determined from the first actual locating trajectory, the second actual locating trajectory, and the third actual locating trajectory.

Optionally, the lesion locating method further includes:

merge, according to the actual positional relationship of the camera and the ultrasound probe, the center line of the ultrasound probe in the reference view as a virtual projection point; and determining the actual locating trajectory, including: determining, according to a positional relationship of the virtual mark point and the virtual projection point in the reference view, a movement direction corresponding to coincidence of the virtual projection point and the virtual mark point, and controlling movement of the ultrasound probe according to the movement direction until the virtual projection point and the virtual mark point coincide with each other in the reference view.

Accordingly, the present disclosure further provides a lesion locating system which locates a lesion by locating a mark on a body surface, and includes:

an image acquisition assembly having an ultrasound probe, and at least one camera distributed on one side or both sides of a sector-scanning plane of the ultrasound probe and fixed in position relative to the ultrasound probe, and a center line of the camera is parallel to a center line of the ultrasound probe;

a reference image display device configured to display a reference view, wherein the reference view is formed according to data acquired in real time by the camera, the reference view has a size of a fixed value, and a virtual mark point corresponding to the mark is formed in the reference view; and a processor, including an actual locating trajectory calculation unit configured to calculate, according to a position of the virtual mark point in the reference view and an actual positional relationship of the camera and the ultrasound probe, an actual locating trajectory that enables the center line of the ultrasound probe to coincide with the mark.

Optionally, the lesion locating system further includes:

a pre-locating instruction input unit configured to input a pre-locating instruction, according to which the image acquisition assembly is moved to a position above the mark; and an actuating mechanism configured to drive the image acquisition assembly to move;

wherein the processor includes a pre-locating processing unit configured to control the actuating mechanism to move according to the pre-locating instruction, judge, after an action corresponding to the pre-locating instruction is completed by the actuating mechanism, whether a current view acquired and formed by the camera contains a virtual mark point corresponding to the mark, and take, if the current view contains the virtual mark point corresponding to the mark, the current view as the reference view.

Optionally, the actual locating trajectory calculation unit has a motion boundary condition calculation subunit for calculating a motion boundary condition, and the motion boundary condition calculation subunit is configured to limit, according to the pre-locating height, a motion boundary condition of the image acquisition assembly so that the ultrasound probe is movable within a preset plane, wherein the preset plane is a plane perpendicular to the center line of the ultrasound probe and corresponding to the pre-locating height.

Optionally, the processor further includes an imaging unit configured to: establish an imaging proportional relation between the current view and an actual acquisition region of the camera, and form the reference view according to the imaging proportional relation;

set a preset value of the pre-locating height, and input a pre-locating instruction so that the pre-locating height is equal to the preset value and the proportional relation is a fixed value;

or establish a calculation model of the imaging proportional relation by taking the preset value of the pre-locating height as a variable, and calculate an actual imaging proportional relation after obtaining a value of the pre-locating height;

or set an installation position of the camera so that part of a side edge contour of the ultrasound probe always exists in the current view acquired by the camera, and calculate, when establishing the imaging proportional relation, the imaging proportional relation from an actual distance from the center line of the camera to the side edge contour and a reference distance in the reference view.

Optionally, the center line of the camera is located on a midperpendicular plane of the sector-scanning plane of the ultrasound probe, so the imaging unit is configured to: form the reference view so that the center line of the camera is located at a center of the reference view, the reference view takes a projection of the midperpendicular plane of the ultrasonic sector-scanning plane as a transverse axis and a direction perpendicular to the transverse axis as a longitudinal direction; and the actual locating trajectory calculation unit includes an actual transverse displacement calculation subunit and an actual longitudinal displacement calculation subunit, wherein the actual longitudinal displacement calculation subunit is configured to: move, according to a position of the virtual mark point in the reference view, the virtual mark point to a virtual longitudinal displacement desired to coincide with the transverse axis, and calculate the actual longitudinal displacement according to the virtual longitudinal displacement and the imaging proportional relation.

Optionally, one camera is provided, and the actual transverse displacement calculation subunit is configured to: calculate a virtual transverse displacement of the virtual mark point according to the position of the virtual mark point in the reference view, and calculate the actual transverse displacement according to the virtual transverse displacement and the imaging proportional relation, wherein
a calculation formula of the virtual transverse displacement satisfies:

$$L_0 = \frac{\arctan\frac{h_1 + h_2}{a} - \frac{\pi - \theta}{2}}{\theta} \times L$$

where $L_0$ is a virtual transverse displacement component, a is a center distance between the ultrasound probe and the camera, $h_1$ is a height distance between the ultrasound probe and the camera, $h_2$ is the pre-locating height, $\theta$ is a viewing angle corresponding to an acquisition region of the camera in the transverse direction, and L is a view width corresponding to the reference view in the transverse direction.

Optionally, two cameras are provided, including a first camera and a second camera, wherein the first camera and the second camera are symmetrically distributed on two sides of the sector-scanning plane of the ultrasound probe, and have a same height difference from the ultrasound probe;

the imaging unit is configured to: form a first reference view from data acquired by the first camera, and form a second reference view from data acquired by the second camera; and the actual transverse displacement calculation subunit is configured to: calculate the actual transverse displacement from a position of the virtual mark point in the first reference view and a position of the virtual mark point in the second reference view, wherein a calculation formula of the actual transverse displacement satisfies:

$$y = \frac{\tan\left(\frac{L_2}{L}\theta\right) - \tan\left(\frac{L_1}{L}\theta\right)}{\tan\left(\frac{L_1}{L}\theta\right) + \tan\left(\frac{L_2}{L}\theta\right)}a$$

where y is an actual transverse displacement component, a is a center distance between the ultrasound probe and each camera, $L_1$ is a transverse distance between the virtual mark point in the first reference view and a view center; and $L_2$ is a transverse distance between the virtual mark point in the second reference view and the view center; images acquired by the first camera and the second camera each have a viewing angle $\theta$ in the transverse direction; and the first reference view and the second reference view each have a preset view width L.

Optionally, two cameras are provided, including a first camera and a second camera, wherein the first camera and the second camera are distributed on two sides of the sector-scanning plane of the ultrasound probe, at least one of the first camera or the second camera has a center line deviating from a midperpendicular plane of the sector-scanning plane of the ultrasound probe, and the first camera and the second camera have a same height difference from the ultrasound probe;

the imaging unit is configured to: form a first reference view from data acquired by the first camera, and form a second reference view from data acquired by the second camera; and the actual locating trajectory calculation unit is configured to: calculate a virtual transverse displacement and a virtual longitudinal displacement according to positions of the virtual mark point in the first reference view and the second reference view; and calculate an actual transverse displacement and an actual longitudinal displacement according to the virtual transverse displacement, the virtual longitudinal displacement and the imaging proportional relation; wherein in calculation of the virtual transverse displacement and the virtual longitudinal displacement, a virtual projection point of the center line of the ultrasound probe is taken as an origin, a virtual sector-scanning projection line of the sector-scanning plane of the ultrasound probe is taken as a Y axis, and a virtual midperpendicular projection line of the midperpendicular plane of the sector-scanning plane of the ultrasound probe is taken as an X axis to establish a coordinate system, and according to the positions of the virtual mark point in the first reference view and the second reference view, a coordinate calculation formula set of the virtual mark point is established:

$$y_1 = (\tan \theta_1)x_1 + b_1 - a_1 \tan \theta_1;$$

$$y_1 = (\tan \theta_2)x_1 + b_2 - a_2 \tan \theta_2;$$

where coordinates of the virtual mark point 41 are $(x_1, y_1)$, $\theta_1$ is an angle between the virtual mark point 41 and the sector-scanning plane of the ultrasound probe (corresponding to the X axis) in the first reference view 4a, a coordinate position of the first camera 21 is $(a_1, b_1)$, a coordinate position of the second camera 22 is $(a_2, b_2)$, and $\theta_2$ is an angle between the virtual mark point 41 and the sector-scanning plane of the ultrasound probe (corresponding to the X axis) in the second reference view 4b.

Optionally, a reference scale is provided in the reference view or on a display device of the reference view, the reference scale has corresponding scale values which are converted into and displayed as size values corresponding to the actual acquisition region of the camera according to an imaging proportion.

Optionally, the lesion locating system is provided with at least two camera groups, each of which includes one or two cameras, each actual locating trajectory calculation unit obtains an actual locating trajectory to be verified according to one camera group, and the processor further includes a verification unit configured to obtain a final actual locating trajectory according to at least two actual locating trajectories to be verified.

Optionally, the processor is further configured to:

merge, according to the actual positional relationship of the camera and the ultrasound probe, the center line of the ultrasound probe in the reference view as a virtual projection point; and determine the actual locating trajectory, including: determining, according to a positional relationship of the virtual mark point and the virtual projection point in the reference view, a movement direction corresponding to coincidence of the virtual projection point and the virtual mark point, and controlling movement of the ultrasound probe according to the movement direction until the virtual projection point and the virtual mark point coincide with each other in the reference view.

According to the lesion locating method and the lesion locating system of the present disclosure, a camera is used to collect camera data and form a reference view which assists the ultrasound probe in rapid locating, so that the difficulty of locating is reduced, the efficiency of lesion locating is increased, and the operation time is saved.

DESCRIPTION OF THE INVENTION

Figure 1:
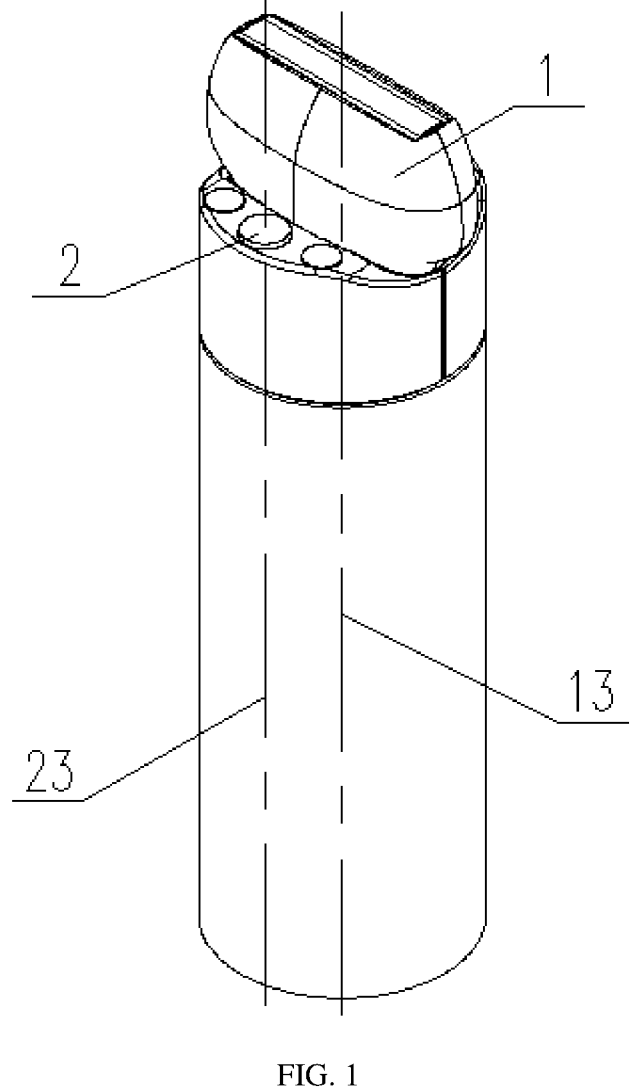
FIG. 1 shows an exemplary structural diagram of an image acquisition assembly using a single camera according to the present disclosure.
Figure 2:
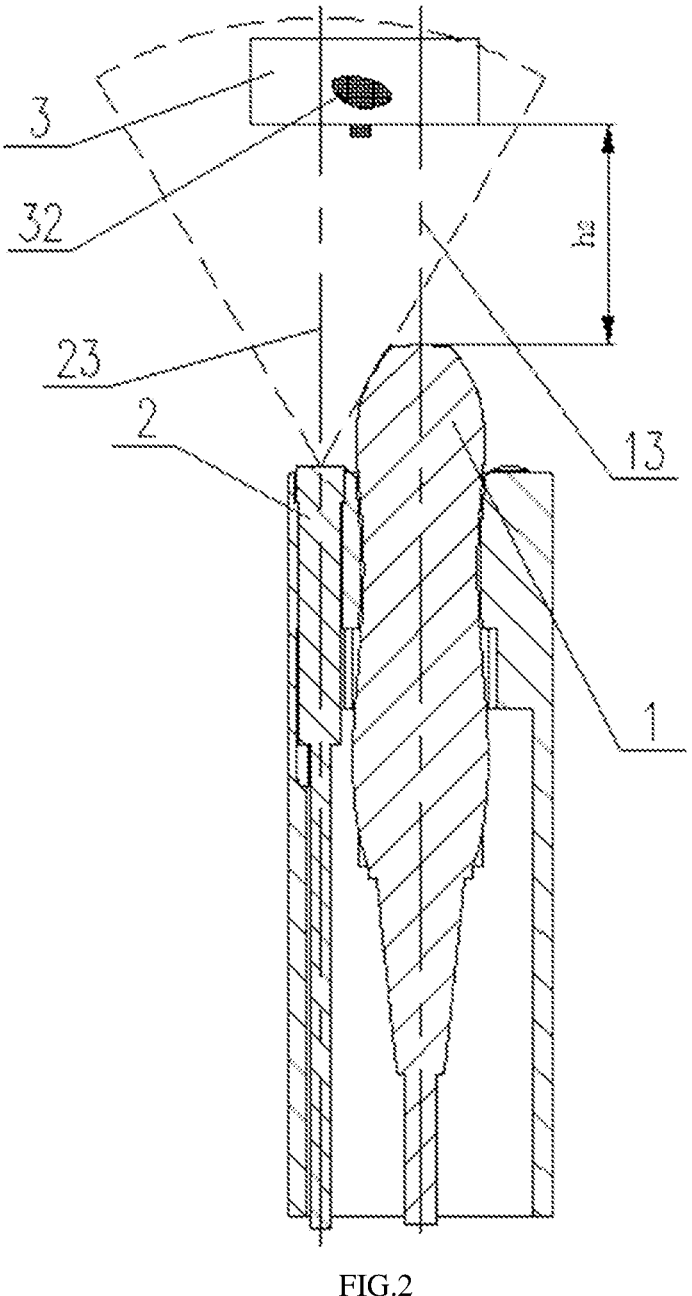
FIG. 2 shows a schematic positional relationship of the image acquisition assembly of FIG. 1 with a mark and a lesion in a front view when the ultrasound probe is positioned at a pre-locating height.
Figure 3:
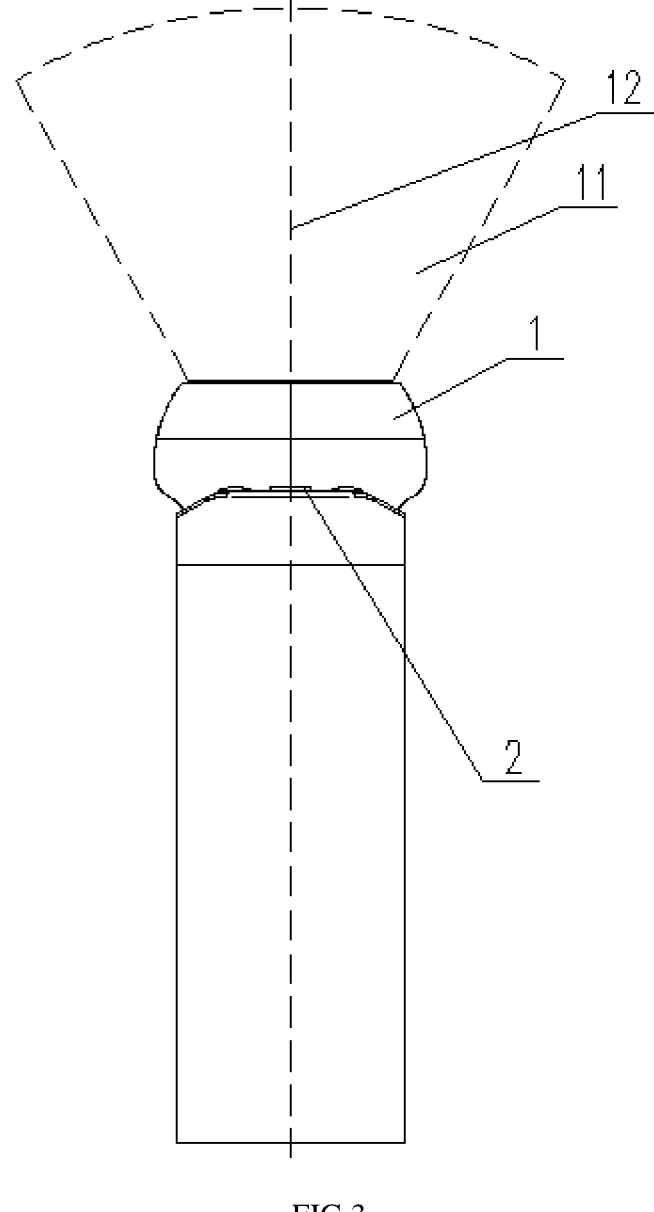
FIG. 3 shows a view of the image acquisition assembly of FIG. 1 in a left-hand view.
Figure 4:
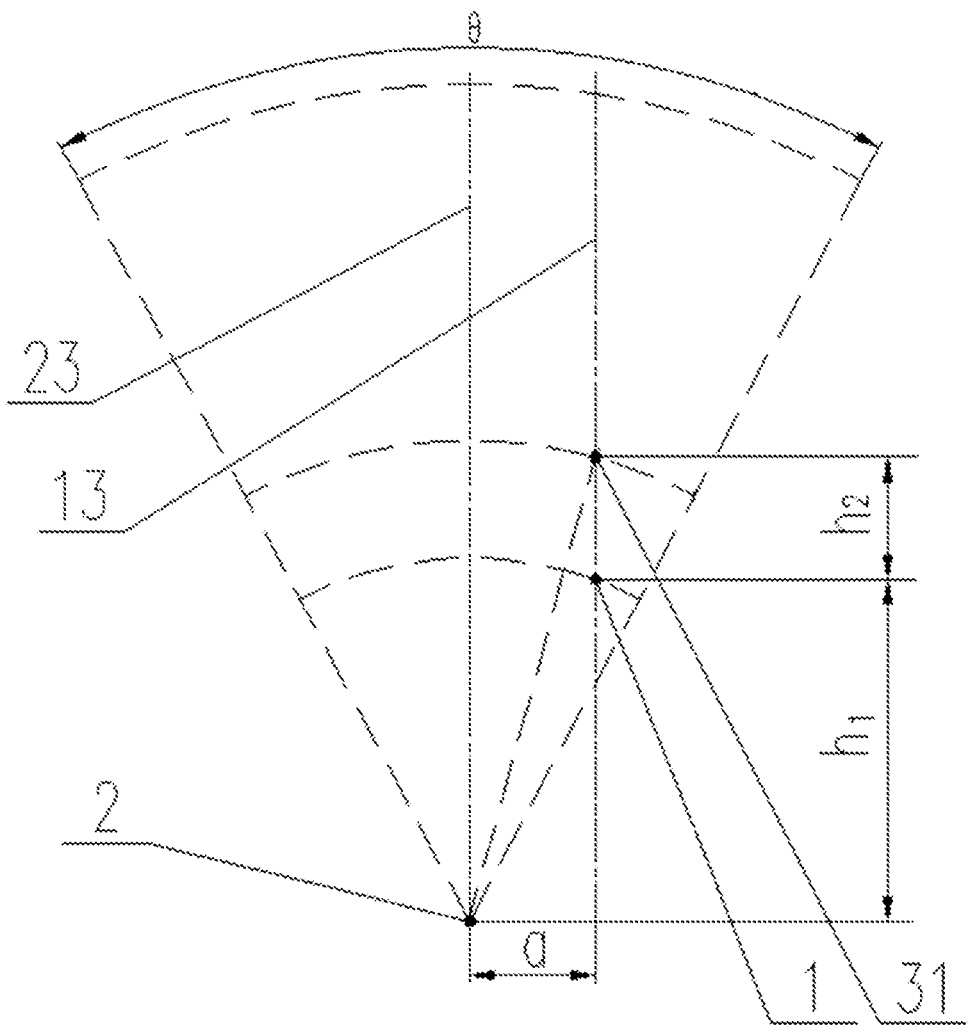
FIG. 4 shows a schematic positional relationship of the ultrasound probe, the camera and the mark when the ultrasound probe of the image acquisition assembly of FIG. 1 is positioned at a pre-locating height.

The following describes implementations of the present disclosure by way of specific embodiments, and other advantages and effects of the present disclosure will be readily apparent to those skilled in the art from the disclosure herein.

It is to be understood that the terms "upper", "lower", "left", "right", "middle", "one" and the like used in the description are for clarity of description only instead of limiting the implementation scope of the present disclosure, and any change or adjustment of the relative relationship between the terms without any substantial technical change should also be regarded as falling into the implementation scope of the present disclosure.

The present disclosure provides a lesion locating method which, referring to FIGS. 1 to 15, involves locating a lesion 32 in a body by locating a mark 31 on a body surface, and using an image acquisition assembly in locating to locate the mark 31, so that a center line 13 of the ultrasound probe 1 coincides with the mark 31. The ultrasound probe 1 is aligned with the mark 31, namely, aligned with the lesion 32. The image acquisition assembly includes an ultrasound probe 1, and at least one camera 2 distributed on one side or both sides of a sector-scanning plane 11 of the ultrasound probe 1 and fixed in position relative to the ultrasound probe 1, and a center line 23 of the camera 2 is parallel to the center line 13 of the ultrasound probe 1. The lesion locating method includes the following steps S1 to S2.

At S1, forming a reference view 4 (including 41, 42) according to data acquired in real time by the camera 2 (including 21, 22), where the reference view 4 has a preset size, and a virtual mark point 41 corresponding to the mark 31 is formed in the reference view 4.

At S2, determining, according to a position of the virtual mark point 41 in the reference view 4 and an actual positional relationship of the camera 2 and the ultrasound probe 1, an actual locating trajectory that enables the center line 13 of the ultrasound probe 1 to coincide with the mark 31.

According to the lesion locating method of the present disclosure, a camera 2 is used to collect camera data and form a reference view 4 which assists the ultrasound probe 1 in rapid locating with a position of a mark 31 in the reference view 4, and after the reference view 4 is formed, the locating can be completed by controlling movement of the image acquisition assembly according to the reference view 4 without any manual operation, which not only reduces the difficulty of locating, but also increases the efficiency of lesion locating, and saves the operation time.

In some embodiments, forming the reference view 4 according to the data acquired in real time by the camera 2 (S1) includes the following steps S101 to S103.

At S101, inputting a pre-locating instruction, according to which the image acquisition assembly is moved to a position above the mark 31.

At S103, judging, when the image acquisition assembly completes the pre-locating instruction, whether a current view acquired and formed by the camera 2 in real time contains a virtual mark point 41 corresponding to the mark 31;

taking, if the current view contains the virtual mark point corresponding to the mark, the current view as the reference view 4 and a current height distance of the ultrasound probe 1 to the mark 31 as a pre-locating height $h_2$, and inputting, if the current view does not contain the virtual mark point corresponding to the mark, the pre-locating instruction again, until the reference view 4 is formed.

In the above and following embodiments, the ultrasound probe 1 is a B-mode ultrasound probe, and the current height distance can be obtained by processing ultrasonic data obtained by the B-mode ultrasound probe. In an ultrasonic view formed by an existing B-mode ultrasound probe, the current height distance can be directly read, and when the current height is obtained in this manner, an acquisition range of the ultrasound probe needs to cover the mark point when the ultrasound probe is positioned at a pre-locating height. Apparently, in practical implementations, other devices may be used to obtain the current height distance, but this method of directly obtaining the current height distance with the ultrasound probe 1 is beneficial to simplifying the device and reducing the cost.

In some embodiments, calculating the actual locating trajectory (S2) further includes the following step S201.

At S201, limiting, according to the pre-locating height $h_2$, a motion boundary condition of the image acquisition assembly so that the ultrasound probe 1 is movable within a preset plane, where the preset plane is a plane perpendicular to the center line 13 of the ultrasound probe 1 and corresponding to the pre-locating height. With this mode of firstly performing high pre-locating and then defining a conveying range of the image acquisition assembly, simplifying the complexity of motion trajectory calculation is facilitated, and the efficiency of lesion locating is greatly increased.

In some embodiments, forming the reference view 4 (S1) includes the following step S102.

At S102, establishing an imaging proportional relation between the current view and an actual acquisition region of the camera 2, and forming the reference view 4 according to the imaging proportional relation. Since the acquisition angle range of the camera 2 is a fixed parameter, when the camera 2 is at a height relatively close to the mark 31, the acquisition region corresponding to the reference view 4 has a relatively small actual area, whereas when the camera 2 is at a height relatively far away from the mark 31, the acquisition region corresponding to the reference view 4 has a relatively large actual area, resulting in an imaging proportion changing with the pre-locating height.

In practical implementations, when the imaging proportional relation is established, a preset value of the pre-locating height may be set, and a pre-locating instruction is input so that the pre-locating height is equal to the preset value and the proportional relation is a fixed value. In other words, before determining the actual locating trajectory, the ultrasound probe 1 is moved to a position with a fixed height difference from the mark 31, which may help to reduce the amount of computational data and implement faster locating. Apparently, in practical implementations, it is also possible to establish a calculation model of the imaging proportional relation by taking the preset value of the pre-locating height as a variable, and calculate an actual imaging proportional relation after obtaining a value of the pre-locating height.

In practical implementations, it is also possible to change an installation position of the camera 2 so that part of a side edge contour 43 (see FIG. 8 or 9) of the ultrasound probe 1 always exists in the current view acquired by the camera 2. Therefore, when establishing the imaging proportional relation, the imaging proportional relation may be calculated from an actual distance from the center line of the camera 2 to the side edge contour and a reference distance in the reference view 4.

The following embodiments specifically describe how to calculate the actual locating trajectory:

In some embodiments, referring to FIGS. 1 to 9, when a center line 23 of the camera 2 is located on the midperpendicular plane 12 of the sector-scanning plane 11 of the ultrasound probe, when the reference view 4 is formed, the center line 23 of the camera 2 is located at a center of the reference view 4, the reference view 4 takes a projection of the midperpendicular plane 12 of the ultrasonic sector-scanning plane 11 as a transverse axis and a direction perpendicular to the transverse axis as a longitudinal direction, and on this condition, calculating the actual locating trajectory includes the following step S202.

At S202, calculating an actual transverse displacement and an actual longitudinal displacement, respectively (including the following steps S2021 and S2022).

At S2021, calculating the actual longitudinal displacement, which includes the following steps S2021a to S2021b.

At S2021a, moving, according to a position of the virtual mark point 41 in the reference view 4, the virtual mark point 41 to a virtual longitudinal displacement desired to coincide with the transverse axis.

At S2021b, calculating the actual longitudinal displacement according to the virtual longitudinal displacement and the imaging proportional relation.

In some embodiments, referring to FIGS. 1 to 5, one camera 2 is provided, then the following step is included:

at S2022, calculating the actual transverse displacement, which includes the following steps S2022a to S2022b.

At S2022a, calculating a virtual transverse displacement of the virtual mark point 41 according to the position of the virtual mark point 41 in the reference view 4.

At S2022a, calculating the actual transverse displacement according to the virtual transverse displacement and the imaging proportional relation.

Specifically, a calculation formula of the virtual transverse displacement satisfies:

$$L_0 = \frac{\arctan\frac{h_1 + h_2}{a} - \frac{\pi - \theta}{2}}{\theta} \times L$$

where $L_0$ is a virtual transverse displacement component, a is a center distance between the ultrasound probe 1 and the camera 2, $h_1$ is a height distance between the ultrasound probe 1 and the camera 2, $h_2$ is the pre-locating height, $\theta$ is a viewing angle corresponding to an acquisition region of the camera 2 in the transverse direction, and L is a view width corresponding to the reference view 4 in the transverse direction.

In practical implementations, the sector-scanning plane 11 of the ultrasound probe 1 may have, but is not limited to, a sector shape.

Figure 5:
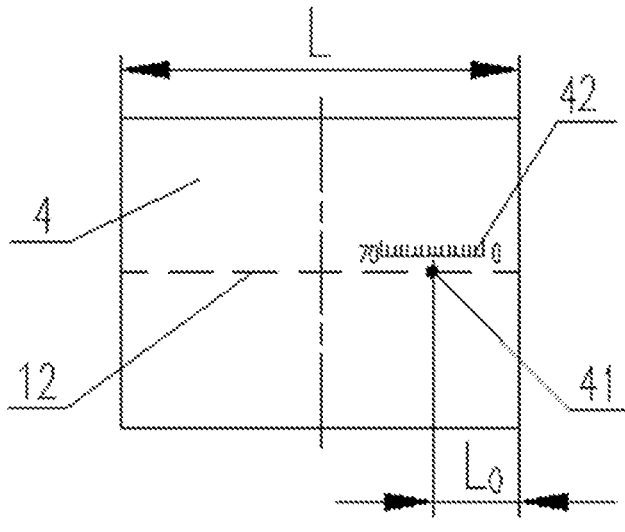
FIG. 5 shows an exemplary reference view formed by the acquisition assembly of FIG. 1.
Figure 6:
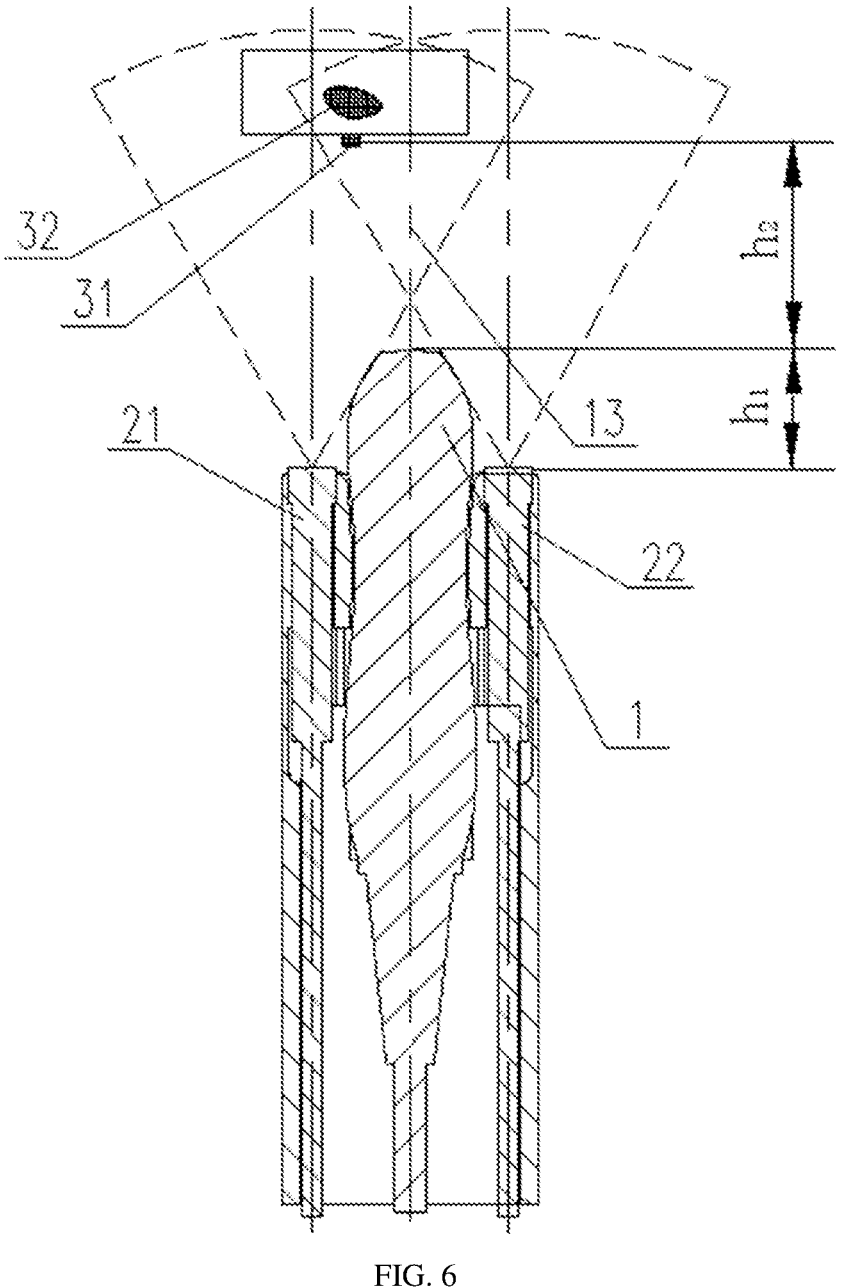
FIG. 6 shows a schematic positional relationship of the image acquisition assembly with the mark and the lesion when the ultrasound probe is positioned at a pre-locating height (with cameras symmetrically arranged)
Figure 7:
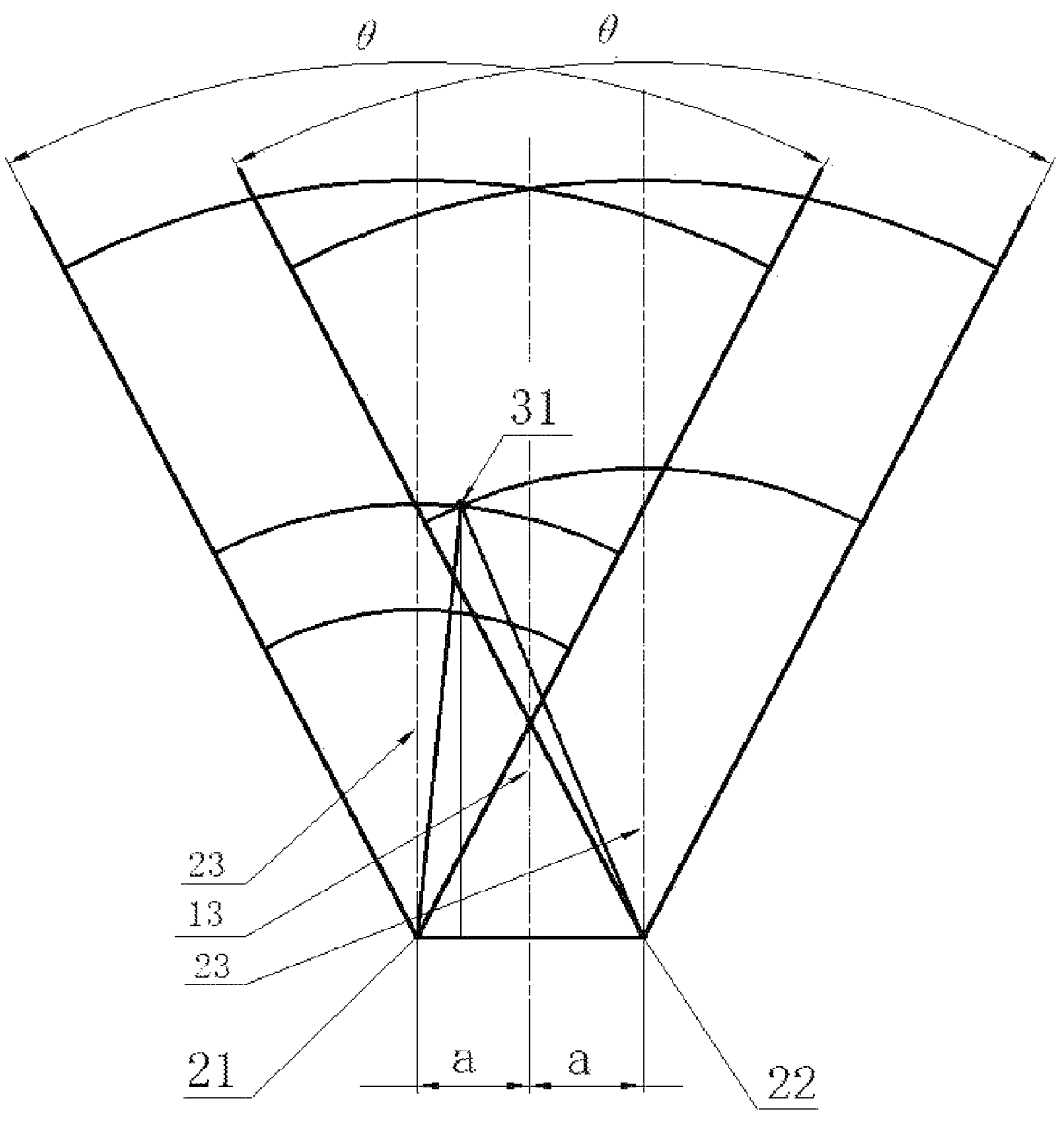
FIG. 7 shows a schematic positional relationship of the ultrasound probe, the camera and the mark in FIG. 6.
Figure 8:
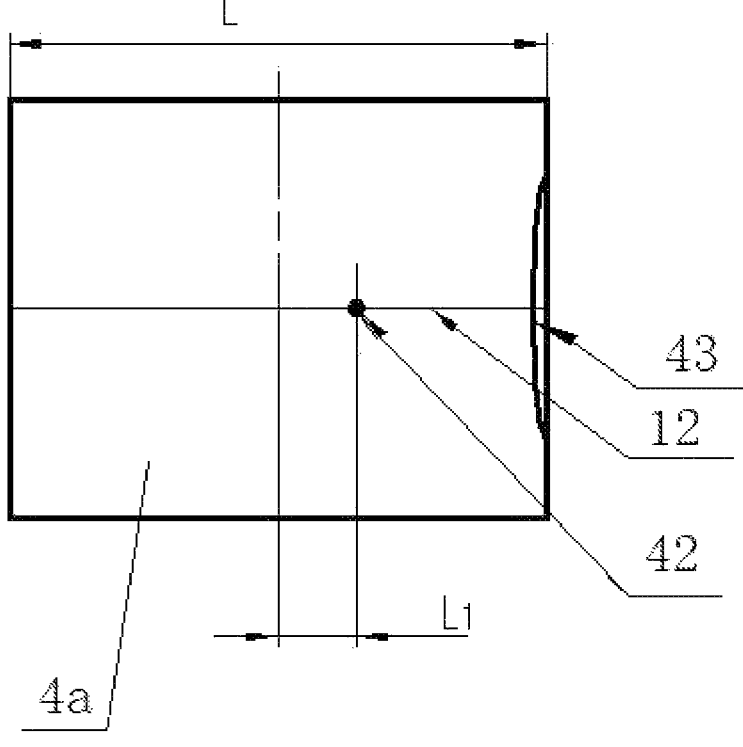
FIG. 8 shows a first reference view correspondingly formed by the image acquisition assembly of FIG. 6.
Figure 9:
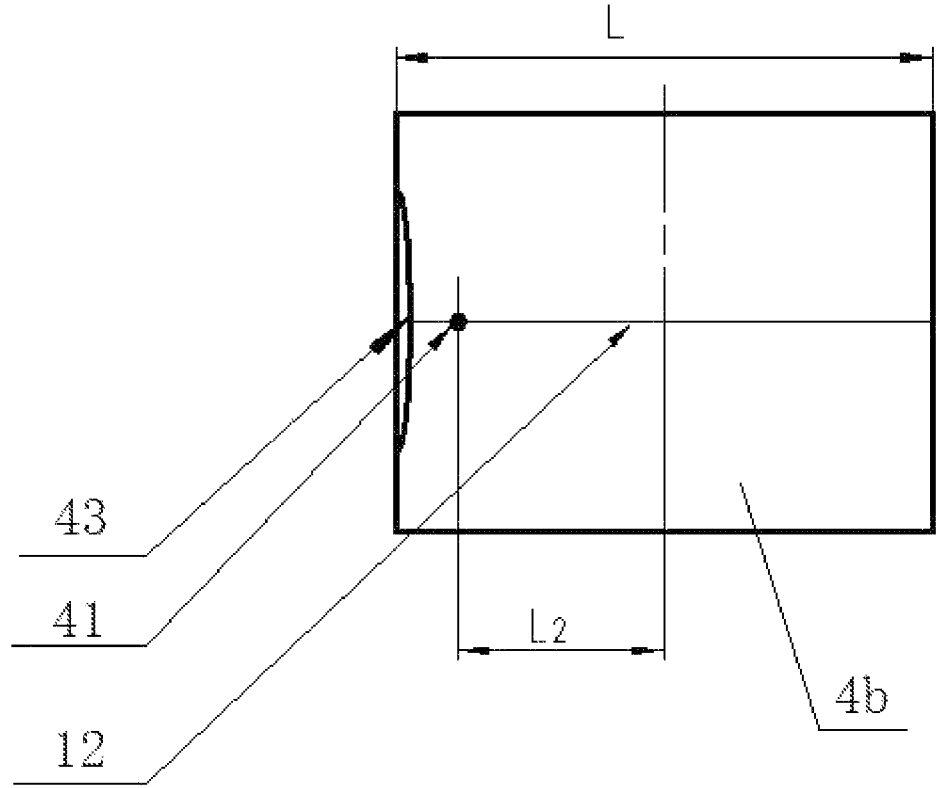
FIG. 9 shows a second reference view correspondingly formed by the image acquisition assembly of FIG. 6.
Figure 10:
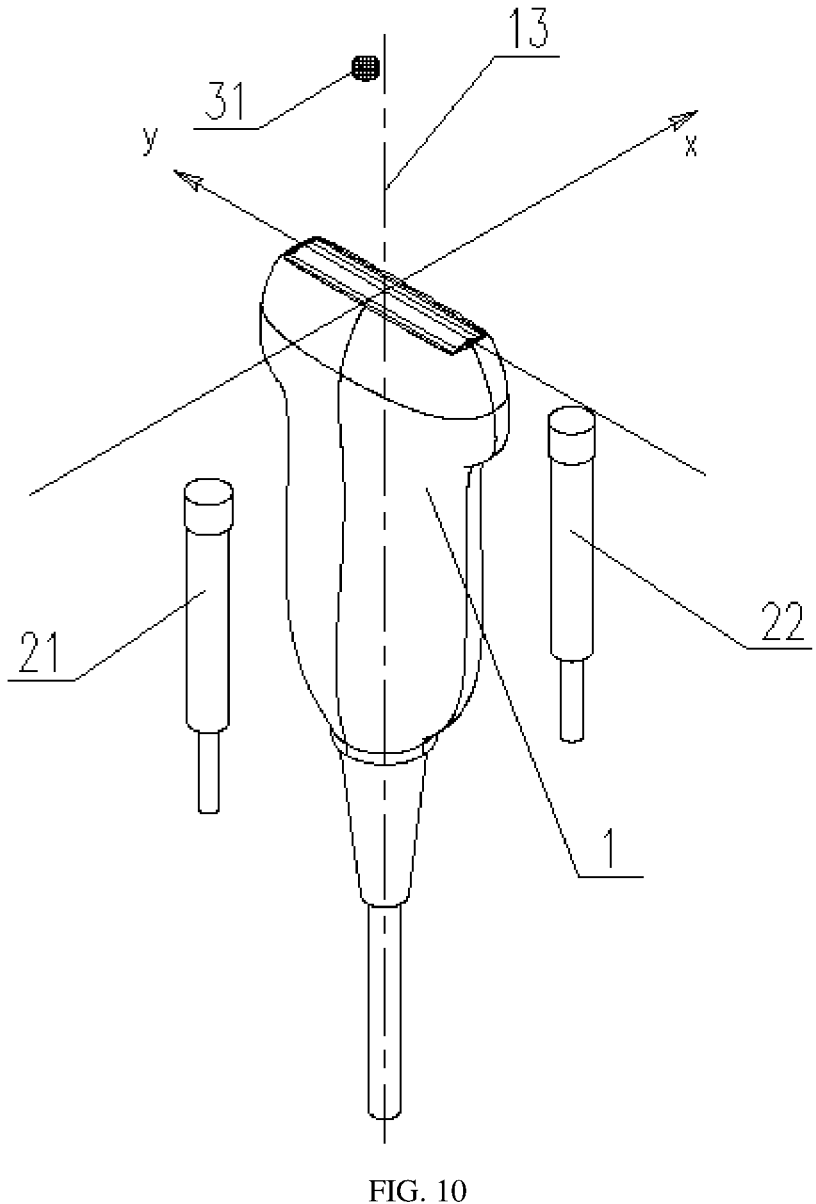
FIG. 10 shows a schematic positional relationship of the image acquisition assembly with the mark and the lesion in a three-dimensional space when the ultrasound probe is positioned at a pre-locating height (with cameras not symmetrically arranged)
Figure 11:
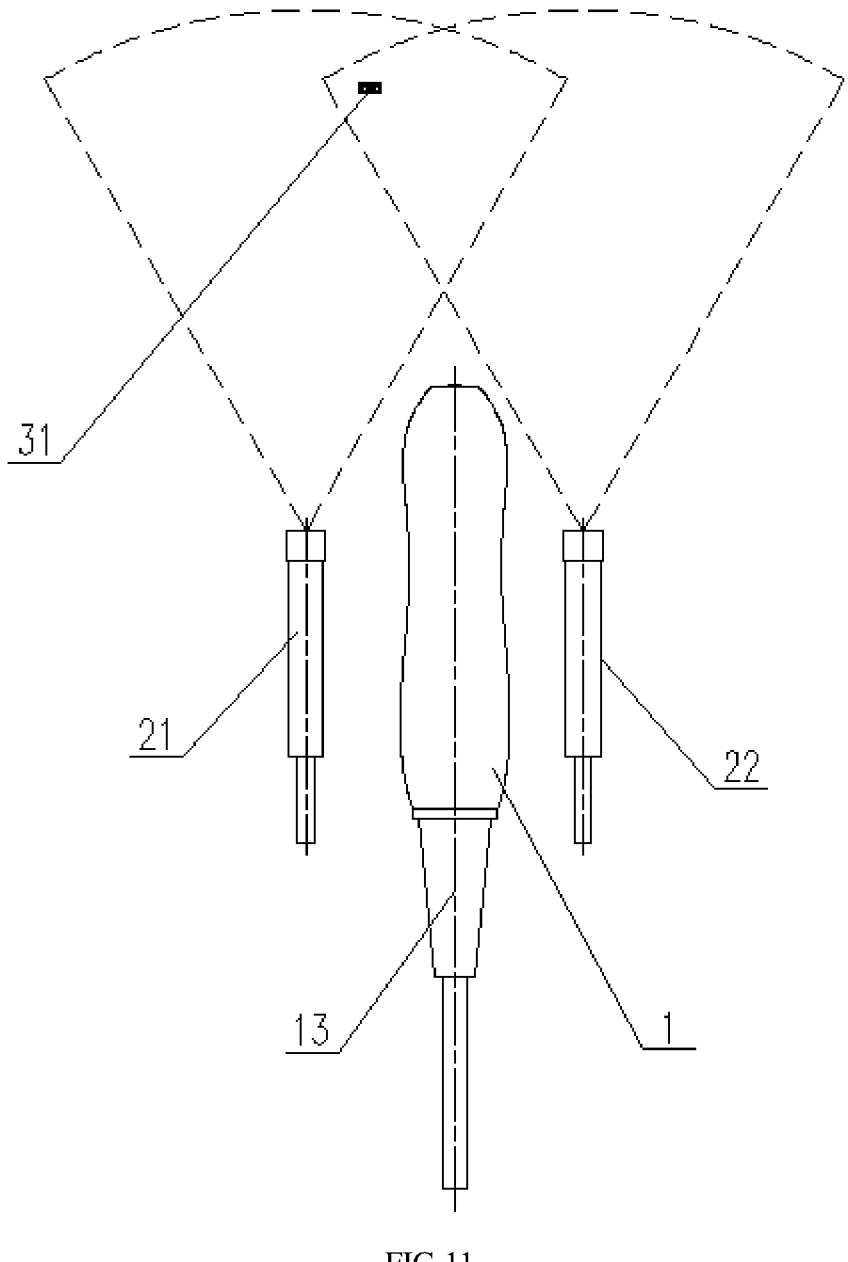
FIG. 11 shows a schematic positional relationship of the image acquisition assembly with the mark and the lesion in a front view when the ultrasound probe is positioned at a pre-locating height (with cameras not symmetrically arranged)
Figure 12:
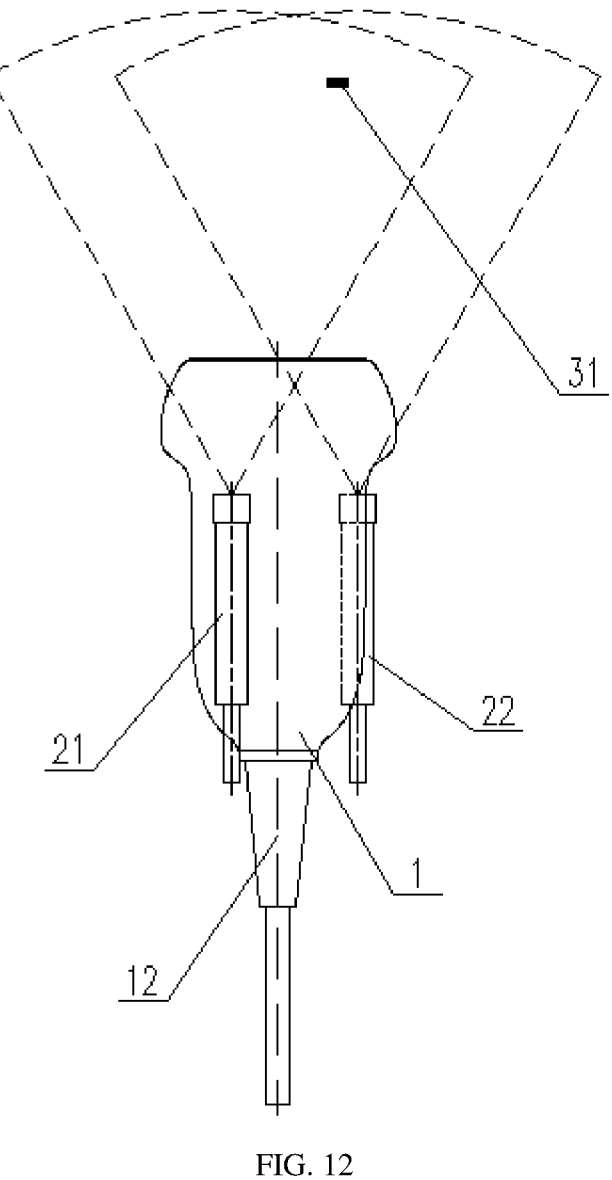
FIG. 12 shows a schematic positional relationship of the image acquisition assembly with the mark and the lesion in a left-hand view when the ultrasound probe is positioned at a pre-locating height (with cameras not symmetrically arranged)
Figure 13:
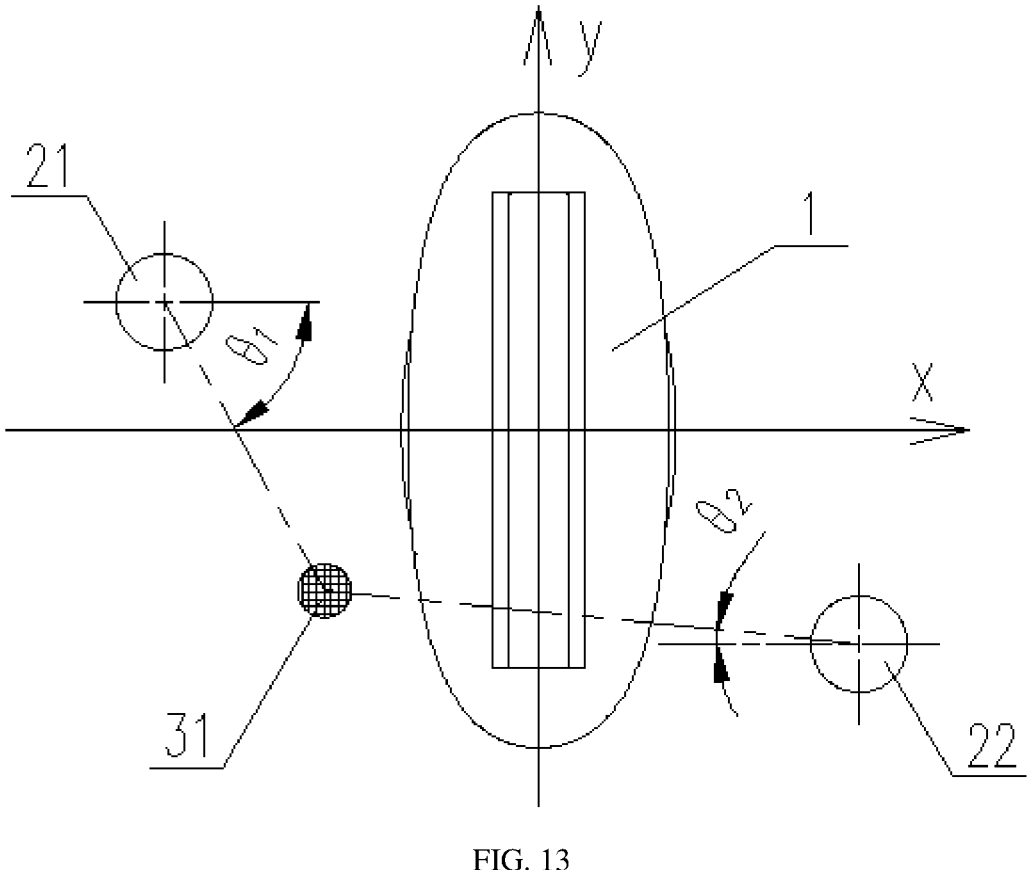
FIG. 13 is a schematic diagram of a coordinate system established with the ultrasound probe as an origin using the image acquisition assembly of FIG. 10.
Figure 14:
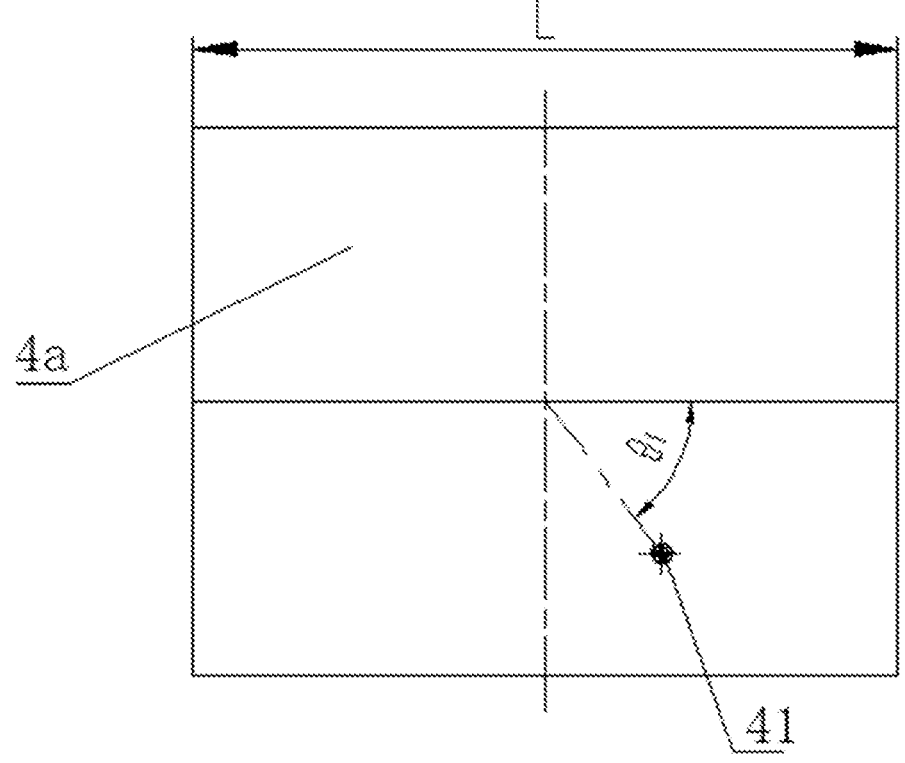
FIG. 14 shows a first reference view correspondingly formed by the image acquisition assembly of FIG. 10.

In some embodiments, a reference scale 42 with fixed position and shape is set corresponding to the reference view. The reference scale 42 has corresponding scale values which are converted into and displayed as size values corresponding to the actual acquisition region of the camera according to an imaging proportion. In FIG. 5, the reference scale 42 is merged and formed into the reference view 4, and the reference scale 42 does not change position with any movement of the image in the display window, or change with the imaging proportion, so that the actual transverse displacement can be visually observed from the scale 42. If the pre-locating height $h_2$ is preset to be a fixed value, the displayed scale value is a fixed value, and the reference scale may be formed in the reference view, or provided on a display screen or any other device for displaying the reference view.

In other embodiments, referring to FIGS. 6 to 9, two cameras 2 are provided, including a first camera 21 and a second camera 22. The first camera 21 and the second camera 22 are symmetrically distributed on two sides of the sector-scanning plane 11 of the ultrasound probe 1, and have a same height difference from the ultrasound probe 1. The first camera 21 acquires data and forms a first reference view 4a (see FIG. 8), and the second camera 22 acquires data and forms a second reference view 4b (see FIG. 9), so:

the step S2022 of calculating the actual transverse displacement includes: calculating the actual transverse displacement from a position of the virtual mark point 41 in the first reference view 4a and a position of the virtual mark point 41 in the second reference view 4b.

Specifically, a calculation formula of the actual transverse displacement satisfies:

$$y = \frac{\tan\left(\frac{L_2}{L}\theta\right) - \tan\left(\frac{L_1}{L}\theta\right)}{\tan\left(\frac{L_1}{L}\theta\right) + \tan\left(\frac{L_2}{L}\theta\right)}a$$

where y is an actual transverse displacement component, a is a center distance between the ultrasound probe 1 and each camera 2, $L_1$ is a transverse distance between the virtual mark point 41 in the first reference view 4a and a view center; and $L_2$ is a transverse distance between the virtual mark point 41 in the second reference view 4b and the view center; images acquired by the first camera 21 and the second camera 22 each have a viewing angle $\theta$ in the transverse direction; and the first reference view 4a and the second reference view 4b each have a preset view width L.

In still other embodiments, referring to FIGS. 10 to 15, also two cameras 2 are provided, including a first camera 21 and a second camera 22, but the first camera 21 and the second camera 22 are distributed on two sides of the sector-scanning plane 11 of the ultrasound probe 1. At least one of the first camera or the second camera has a center line deviating from a midperpendicular plane of the sector-scanning plane of the ultrasound probe, and the first camera 21 and the second camera 22 have a same height difference from the ultrasound probe 1. The first camera 21 acquires data and forms a first reference view 4a, and the second camera 22 acquires data and forms a second reference view 4b, so:

the step S202 of calculating the actual locating trajectory includes the following steps S2021 to S2022.

Figure 15:
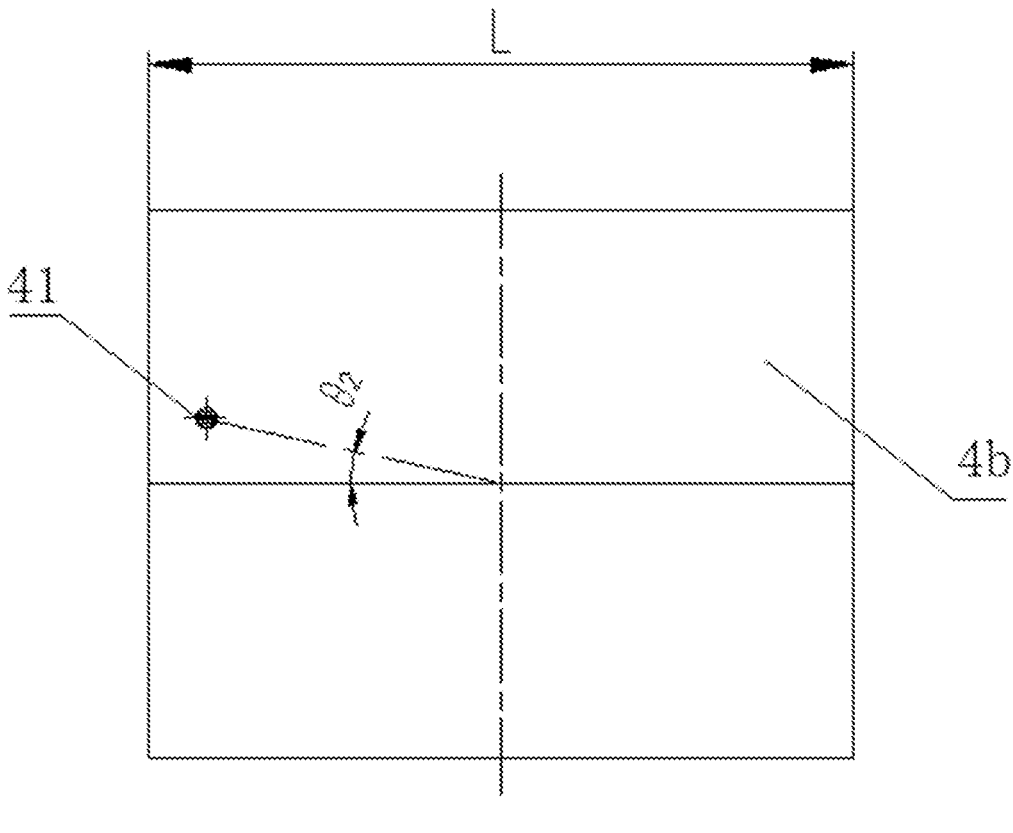
FIG. 15 shows a second reference view correspondingly formed by the image acquisition assembly of FIG. 10.

At S2021, calculating a virtual transverse displacement and a virtual longitudinal displacement according to positions of the virtual mark point 41 in the first reference view 4a (FIG. 14) and the second reference view 4b (FIG. 15).

At S2022, calculating an actual transverse displacement and an actual longitudinal displacement according to the virtual transverse displacement, the virtual longitudinal displacement and the imaging proportional relation.

In this method, the first camera 21 and the second camera 22 are disposed at flexible positions relative to the ultrasound probe 1, so as to avoid other devices in use, and be applicable in a wider range.

Specifically, in S2021, in calculation of the virtual transverse displacement and the virtual longitudinal displacement, a virtual projection point of the center line 13 of the ultrasound probe 1 is taken as an origin, a virtual sector-scanning projection line of the sector-scanning plane 11 of the ultrasound probe is taken as a Y axis, and a virtual midperpendicular projection line of the midperpendicular plane 12 of the sector-scanning plane 11 of the ultrasound probe is taken as an X axis to establish a coordinate system, and according to the positions of the virtual mark point 41 in the first reference view 4*a* and the second reference view 4*b*, a coordinate calculation formula set of the virtual mark point 41 is established:

$$y_1 = (\tan \theta_1)x_1 + b_1 - a_1 \tan \theta_1;$$

$$y_1 = (\tan \theta_2)x_1 + b_2 - a_2 \tan \theta_2;$$

where coordinates of the virtual mark point 41 are $(x_1, y_1)$, $\theta_1$ is an angle between the virtual mark point 41 and the sector-scanning plane of the ultrasound probe (corresponding to the X axis) in the first reference view 4*a*, a coordinate position of the first camera 21 is $(a_1, b_1)$, a coordinate position of the second camera 22 is $(a_2, b_2)$, and $\theta_2$ is an angle between the virtual mark point 41 and the sector-scanning plane of the ultrasound probe (corresponding to the X axis) in the second reference view 4*b*.

In practical implementations, cameras may be divided into at least two camera groups, each of which includes one or two cameras, an actual locating trajectory to be verified is formed according to a reference view acquired and formed by a camera group, and a final actual locating trajectory is obtained according to at least two actual locating trajectories to be verified.

Specifically, in some embodiments, at least two cameras are provided, including a first camera and a second camera, where the first camera and the second camera are symmetrically distributed on two sides of the sector-scanning plane of the ultrasound probe, and each have a center line on a midperpendicular plane of the sector-scanning plane of the ultrasound probe and a same height difference from the ultrasound probe. While locating a lesion, a first actual locating trajectory is calculated from a corresponding first reference view or second reference view formed by the first camera or the second camera, that is, determined from a single camera; a second actual locating trajectory is calculated from corresponding reference views formed by the first camera and the second camera, that is, determined from two cameras, and then a final actual locating trajectory is determined from the first actual locating trajectory and the second actual locating trajectory.

In other embodiments, at least two cameras are provided, including a first camera and a second camera, where the first camera and the second camera are distributed on two sides of the sector-scanning plane of the ultrasound probe, a center line of the first camera is located on the midperpendicular plane of the sector-scanning plane of the ultrasound probe, while a center line of the second camera deviates from the midperpendicular plane of the sector-scanning plane of the ultrasound probe, the first camera and the second camera have a same height difference from the ultrasound probe, and while locating a lesion, a first actual locating trajectory is calculated from a corresponding reference view formed by the first camera, a second actual locating trajectory is calculated from corresponding reference views formed by the two cameras, and a final actual locating trajectory is determined from the first actual locating trajectory and the second actual locating trajectory.

In still other embodiments, at least three cameras are provided, including a first camera, a second camera and a third camera, where the first camera and the third camera are distributed on one side of the sector-scanning plane of the ultrasound probe, the second camera is distributed on the other side of the sector-scanning plane of the ultrasound probe, a center line of the third camera is located on the midperpendicular plane of the sector-scanning plane of the ultrasound probe, while center lines of the first camera and the second camera deviate from the midperpendicular plane of the sector-scanning plane of the ultrasound probe, the first camera, the second camera and the third camera have a same height difference from the ultrasound probe, and while locating a lesion, a first actual locating trajectory is calculated from a corresponding reference view formed by the third camera, a second actual locating trajectory is calculated from corresponding first reference view and second reference view formed by the first camera and the second camera, and a final actual locating trajectory is determined from the first actual locating trajectory and the second actual locating trajectory.

In still other embodiments, at least four cameras are provided, including a first camera, a second camera, a third camera and a fourth camera, where the first camera and the second camera are symmetrically distributed on two sides of the sector-scanning plane of the ultrasound probe, and each have a center line on the midperpendicular plane of the sector-scanning plane of the ultrasound probe, while the third camera and the fourth camera are distributed on two sides of the sector-scanning plane of the ultrasound probe, and each have a center line deviating from the midperpendicular plane of the sector-scanning plane of the ultrasound probe, a first actual locating trajectory is calculated from corresponding reference views formed by the first camera and the second camera, a second actual locating trajectory is calculated from corresponding reference views formed by the third camera and the fourth camera, and a final actual locating trajectory is determined from the first actual locating trajectory and the second actual locating trajectory.

In some further embodiments, at least four cameras are provided, including a first camera, a second camera, a third camera and a fourth camera, where the first camera and the second camera are symmetrically distributed on two sides of the sector-scanning plane of the ultrasound probe, and each have a center line on the midperpendicular plane of the sector-scanning plane of the ultrasound probe, while the third camera and the fourth camera are distributed on two sides of the sector-scanning plane of the ultrasound probe, and each have a center line deviating from the midperpendicular plane of the sector-scanning plane of the ultrasound probe, a first actual locating trajectory is calculated from corresponding reference views formed by the first camera and the second camera, a second actual locating trajectory is calculated from corresponding reference views formed by the third camera and the fourth camera, a third actual locating trajectory is calculated from a corresponding reference view formed by the first camera or the second camera, and a final actual locating trajectory is determined from the first actual locating trajectory, the second actual locating trajectory, and the third actual locating trajectory.

When the final actual locating trajectory is determined according to locating trajectories to be verified (the first actual locating trajectory, the second actual locating trajectory or the third actual locating trajectory), if a difference value of any locating trajectory to be verified is greater than a preset threshold, an abnormal warning signal may be given; and if the difference value of each locating trajectory to be verified is smaller than or equal to the preset threshold, the locating trajectories to be verified are averaged to obtain an average value which is taken as the final actual locating trajectory.

In the above embodiments, the actual locating trajectory is determined through calculation, and then the movement of the ultrasound probe 1, and thus of the whole image acquisition assembly, is controlled according to the calculated actual locating trajectory. In practical implementations, the actual locating trajectory may not be calculated, and instead, the center line 13 of the ultrasound probe 1 is merged into the reference view 4 as a virtual projection point according to an actual positional relationship between the camera 2 and the ultrasound probe 1, then according to a positional relationship of the virtual mark point 41 and the virtual projection point in the reference view 4, a movement direction corresponding to coincidence of the virtual projection point and the virtual mark point 41 is determined, and the ultrasound probe 1 (that is, the whole image acquisition assembly) is controlled to move according to the movement direction, until the virtual projection point and the virtual mark point 41 coincide with each other in the reference view 4. When the virtual projection point is formed by merging in the reference view 4, the center line 23 of the camera 2 corresponds to a center position of the reference view on the reference view 4, the center line 13 of the ultrasound probe 1 has an orientation corresponding to the center line of the camera 2, and the virtual projection point has a direction corresponding to the virtual mark point 41, while orientations of the center line 13 of the ultrasound probe 1 and the center line of the camera 2, and a distance between the virtual projection point and the virtual mark point 41 are determined according to the imaging proportion.

Accordingly, the present disclosure further provides a lesion locating system which locates a lesion by locating a mark 31 on a body surface. The detailed method for locating a lesion with the lesion locating system and the effect obtained thereby may refer to related description of the lesion locating method. The lesion locating system of the present disclosure includes:

an image acquisition assembly having an ultrasound probe 1, and at least one camera 2 distributed on one side or both sides of a sector-scanning plane 11 of the ultrasound probe 1 and fixed in position relative to the ultrasound probe 1, and a center line 23 of the camera 2 is parallel to a center line 13 of the ultrasound probe 1;

a reference view display device (not shown) configured to display a reference view 4, where the reference view 4 is formed according to data acquired in real time by the camera 2, the reference view 4 has a size of a fixed value, and a virtual mark point 41 corresponding to the mark 31 is formed in the reference view 4; and a processor (not shown), including an actual locating trajectory calculation unit configured to calculate, according to a position of the virtual mark point 41 in the reference view 4 and an actual positional relationship of the camera 2 and the ultrasound probe 1, an actual locating trajectory that enables the center line 13 of the ultrasound probe 1 to coincide with the mark 31.

In practical implementations, the processor may be a general purpose processor, including a central processing unit (CPU), a network processor (NP), or the like; or may be a digital signal processor (DSP), an application specific integrated circuit (ASIC), a field-programmable gate array (FPGA) or any other programmable logic device, a discrete gate or a transistor logic device, or a discrete hardware component.

In some embodiments, the lesion locating system further includes:

a pre-locating instruction input unit configured to input a pre-locating instruction, according to which the image acquisition assembly is moved to a position above the mark 31; and an actuating mechanism configured to drive the image acquisition assembly to move.

The processor includes a pre-locating processing unit configured to control the actuating mechanism to move according to the pre-locating instruction, judge, after an action corresponding to the pre-locating instruction is completed by the actuating mechanism, whether a current view acquired and formed by the camera 2 contains a virtual mark point 41 corresponding to the mark 31, and take, if the current view contains the virtual mark point 41 corresponding to the mark 31, the current view as the reference view 4.

In some embodiments, the actual locating trajectory calculation unit has a motion boundary condition calculation subunit for calculating a motion boundary condition, and the motion boundary condition calculation subunit is configured to limit, according to the pre-locating height, a motion boundary condition of the image acquisition assembly so that the ultrasound probe 1 is movable within a preset plane. The preset plane is a plane perpendicular to the center line 13 of the ultrasound probe 1 and corresponding to the pre-locating height.

In some embodiments, the processor further includes an imaging unit configured to: establish an imaging proportional relation between the current view and an actual acquisition region of the camera 2, and form the reference view 4 according to the imaging proportional relation.

In practical implementations, when the imaging proportional relation is established, a preset value of the pre-locating height may be set, and a pre-locating instruction is input so that the pre-locating height is equal to the preset value and the proportional relation is a fixed value. In other words, before determining the actual locating trajectory, the ultrasound probe 1 is moved to a position with a fixed height difference from the mark 31, which may help to reduce the amount of computational data and implement faster locating. Apparently, in practical implementations, it is also possible to establish a calculation model of the imaging proportional relation by taking the preset value of the pre-locating height as a variable, and calculate an actual imaging proportional relation after obtaining a value of the pre-locating height.

In practical implementations, it is also possible to change an installation position of the camera 2 so that part of a side edge contour of the ultrasound probe 1 always exists in the current view acquired by the camera 2. Therefore, when establishing the imaging proportional relation, the imaging proportional relation is calculated from an actual distance from the center line of the camera 2 to the side edge contour and a reference distance in the reference view 4.

In some embodiments, the center line 23 of the camera 2 is located on a midperpendicular plane 12 of the sector-scanning plane 11 of the ultrasound probe, so the imaging unit is configured to: form the reference view 4 so that the center line 23 of the camera 2 is located at a center of the reference view 4, the reference view 4 takes a projection of the midperpendicular plane 12 of the ultrasonic sector-scanning plane 11 as a transverse axis and a direction perpendicular to the transverse axis as a longitudinal direction; and the actual locating trajectory calculation unit includes an actual transverse displacement calculation subunit and an actual longitudinal displacement calculation subunit, where the actual longitudinal displacement calculation subunit is configured to: move, according to a position of the virtual mark point 41 in the reference view 4, the virtual mark point 41 to a virtual longitudinal displacement desired to coincide with the transverse axis, and calculate the actual longitudinal displacement according to the virtual longitudinal displacement and the imaging proportional relation.

In some embodiments, one camera 2 is provided, and the actual transverse displacement calculation subunit is configured to: calculate a virtual transverse displacement of the virtual mark point 41 according to the position of the virtual mark point 41 in the reference view 4, and calculate the actual transverse displacement according to the virtual transverse displacement and the imaging proportional relation, where a calculation formula of the virtual transverse displacement satisfies:

$$L_0 = \frac{\arctan\dfrac{h_1 + h_2}{a} - \dfrac{\pi - \theta}{2}}{\theta} \times L$$

where $L_0$ is a virtual transverse displacement component, $a$ is a center distance between the ultrasound probe 1 and the camera 2, $h_1$ is a height distance between the ultrasound probe 1 and the camera 2, $h_2$ is the pre-locating height, $\theta$ is a viewing angle corresponding to an acquisition region of the camera 2 in the transverse direction, and L is a view width corresponding to the reference view 4 in the transverse direction.

In some embodiments, referring to FIG. 5, a reference scale with fixed position and shape is provided in the reference view 4, and the reference scale 42 has corresponding scale values which are converted into and displayed as size values corresponding to the actual acquisition region of the camera according to an imaging proportion. In practical implementations, the reference scale may be provided on the reference view display device.

In some embodiments, two cameras 2 are provided, including a first camera 21 and a second camera 22. The first camera 21 and the second camera 22 are symmetrically distributed on two sides of the sector-scanning plane 11 of the ultrasound probe 1, and have a same height difference from the ultrasound probe 1.

The imaging unit is configured to: form a first reference view 4a from data acquired by the first camera 21, and form a second reference view 4b from data acquired by the second camera 22; and the actual transverse displacement calculation subunit is configured to: calculate the actual transverse displacement from a position of the virtual mark point 41 in the first reference view 4a and a position of the virtual mark point 41 in the second reference view 4b, where a calculation formula of the actual transverse displacement satisfies:

$$y = \frac{\tan\left(\dfrac{L_2}{L}\theta\right) - \tan\left(\dfrac{L_1}{L}\theta\right)}{\tan\left(\dfrac{L_1}{L}\theta\right) + \tan\left(\dfrac{L_2}{L}\theta\right)}a$$

where y is an actual transverse displacement component, $a$ is a center distance between the ultrasound probe 1 and each camera 2, $L_1$ is a transverse distance between the virtual mark point 41 in the first reference view 4a and a view center; and $L_2$ is a transverse distance between the virtual mark point 41 in the second reference view 4b and the view center; images acquired by the first camera 21 and the second camera 22 each have a viewing angle $\theta$ in the transverse direction; and the first reference view 4a and the second reference view 4b each have a preset view width L.

In some embodiments, two cameras 2 are provided, including a first camera 21 and a second camera 22. The first camera 21 and the second camera 22 are distributed on two sides of the sector-scanning plane 11 of the ultrasound probe 1, at least one of the first camera or the second camera has a center line deviating from a midperpendicular plane of the sector-scanning plane of the ultrasound probe, and the first camera 21 and the second camera 22 have a same height difference from the ultrasound probe 1. At this time, the first camera 21 and the second camera 22 are disposed at flexible positions relative to the ultrasound probe 1, so as to avoid other devices in use, and be applicable in a wider range.

At this time, the imaging unit is configured to: form a first reference view 4a from data acquired by the first camera 21, and form a second reference view 4b from data acquired by the second camera 22; and the actual locating trajectory calculation unit is configured to: calculate a virtual transverse displacement and a virtual longitudinal displacement according to positions of the virtual mark point 41 in the first reference view 4a and the second reference view 4b; and calculate an actual transverse displacement and an actual longitudinal displacement according to the virtual transverse displacement, the virtual longitudinal displacement and the imaging proportional relation.

In calculation of the virtual transverse displacement and the virtual longitudinal displacement, a virtual projection point of the center line of the ultrasound probe 1 is taken as an origin, a virtual sector-scanning projection line of the sector-scanning plane 11 of the ultrasound probe is taken as a Y axis, and a virtual midperpendicular projection line of the midperpendicular plane 12 of the sector-scanning plane 11 of the ultrasound probe is taken as an X axis to establish a coordinate system, and according to the positions of the virtual mark point 41 in the first reference view 4a and the second reference view 4b, a coordinate calculation formula set of the virtual mark point 41 is established:

$$y_1 = (\tan\theta_1)x_1 + b_1 - a_1\tan\theta_1;$$

$$y_1 = (\tan\theta_2)x_1 + b_2 - a_2\tan\theta_2;$$

where coordinates of the virtual mark point 41 are $(x_1, y_1)$, $\theta_1$ is an angle between the virtual mark point 41 and the sector-scanning plane of the ultrasound probe (corresponding to the X axis) in the first reference view 4a, a coordinate position of the first camera 21 is $(a_1, b_1)$, a coordinate position of the second camera 22 is $(a_2, b_2)$, and $\theta_2$ is an angle between the virtual mark point 41 and the sector-scanning plane of the ultrasound probe (corresponding to the X axis) in the second reference view 4b.

In some embodiments, the lesion locating system is provided with multiple camera groups, each of which includes one or two cameras, each actual locating trajectory calculation unit obtains an actual locating trajectory to be verified according to one camera group, and the processor further includes a verification unit configured to obtain a final actual locating trajectory according to at least two actual locating trajectories to be verified.

In some embodiments, the processor is further configured to:

merge, according to the actual positional relationship of the camera and the ultrasound probe, the center line of the ultrasound probe in the reference view as a virtual projection point; and determine the actual locating trajectory, including: determining, according to a positional relationship of the virtual mark point and the virtual projection point in the reference view, a movement direction corresponding to coincidence of the virtual projection point and the virtual mark point, and controlling movement of the ultrasound probe according to the movement direction until the virtual projection point and the virtual mark point coincide with each other in the reference view.

It should be understood that the sequence numbers of the steps in the foregoing embodiments do not imply an order of execution, and the order of execution of each process should be determined by their functions and inherent logic, and should not form any limitation to the implementation process of the embodiments of the present disclosure.

The foregoing embodiments are merely for illustration of the principles and utilities of the present disclosure, but are not intended to limit the present disclosure. Those skilled in the art can modify or change the above embodiments without departing from the spirit and scope of the present disclosure. Accordingly, it is intended that all equivalent modifications or changes which may be made by those of ordinary skill in the art without departing from the spirit and scope of the present disclosure are covered by the appended claims.

What is claimed is:

1. A lesion locating method, comprising locating a lesion by locating a mark on a body surface; using an image acquisition assembly in locating to locate the mark, wherein the image acquisition assembly comprises an ultrasound probe, and at least one camera distributed on one side or both sides of a sector-scanning plane of the ultrasound probe and fixed in position relative to the ultrasound probe, and a center line of the camera is parallel to a center line of the ultrasound probe, and the lesion locating method comprises:

forming a reference view according to data acquired in real time by the camera, wherein the reference view has a preset size, and a virtual mark point corresponding to the mark is formed in the reference view; and according to a position of the virtual mark point in the reference view and an actual positional relationship of the camera and the ultrasound probe, determining an actual locating trajectory that enables the center line of the ultrasound probe to coincide with the mark.

2. The lesion locating method according to claim 1, wherein forming the reference view according to the data acquired in real time by the camera comprises:

inputting a pre-locating instruction, according to which the image acquisition assembly is moved to a position above the mark; and judging, when the image acquisition assembly completes the pre-locating instruction, whether a current view acquired and formed by the camera in real time contains a virtual mark point corresponding to the mark;

taking, if the current view contains the virtual mark point corresponding to the mark, the current view as the reference view and a current height distance of the ultrasound probe to the mark as a pre-locating height, and inputting, if the current view does not contain the virtual mark point corresponding to the mark, the pre-locating instruction again, until the reference view is formed.

3. The lesion locating method according to claim 2, wherein calculating the actual locating trajectory further comprises:

limiting, according to the pre-locating height, a motion boundary condition of the image acquisition assembly so that the ultrasound probe is movable within a preset plane, wherein the preset plane is a plane perpendicular to the center line of the ultrasound probe and corresponding to the pre-locating height.

4. The lesion locating method according to claim 2, wherein forming the reference view comprises: establishing an imaging proportional relation between the current view and an actual acquisition region of the camera, and forming the reference view according to the imaging proportional relation;

setting a preset value of the pre-locating height, and inputting a pre-locating instruction so that the pre-locating height is equal to the preset value and the proportional relation is a fixed value;

or establishing a calculation model of the imaging proportional relation by taking the preset value of the pre-locating height as a variable, and calculating an actual imaging proportional relation after obtaining a value of the pre-locating height;

or setting an installation position of the camera so that part of a side edge contour of the ultrasound probe always exists in the current view acquired by the camera, and calculating, when establishing the imaging proportional relation, the imaging proportional relation from an actual distance from the center line of the camera to the side edge contour and a reference distance in the reference view.

5. The lesion locating method according to claim 4, wherein when the center line of the camera is located on a midperpendicular plane of the sector-scanning plane of the ultrasound probe and the reference view is formed, the center line of the camera is located at a center of the reference view, the reference view takes a projection of the midperpendicular plane of the ultrasonic sector-scanning plane as a transverse axis and a direction perpendicular to the transverse axis as a longitudinal direction, and calculating the actual locating trajectory comprises: calculating an actual transverse displacement and an actual longitudinal displacement, respectively, wherein calculating the actual longitudinal displacement comprises:

moving, according to a position of the virtual mark point in the reference view, the virtual mark point to a virtual longitudinal displacement desired to coincide with the transverse axis, and calculating the actual longitudinal displacement according to the virtual longitudinal displacement and the imaging proportional relation.

6. The lesion locating method according to claim 5, wherein at least one camera is provided, the actual locating trajectory is calculated from a reference view formed by a single camera, and calculating the actual transverse displacement comprises: calculating a virtual transverse displacement of the virtual mark point according to the position of the virtual mark point in the reference view, and calculating the actual transverse displacement according to the virtual transverse displacement and the imaging proportional relation, wherein a calculation formula of the virtual transverse displacement satisfies:

$$L_0 = \frac{\arctan\frac{h_1 + h_2}{a} - \frac{\pi - \theta}{2}}{\theta} \times L$$

where $L_0$ is a virtual transverse displacement component, a is a center distance between the ultrasound probe and the camera, $h_1$ is a height distance between the ultrasound probe and the camera, $h_2$ is the pre-locating height, $\theta$ is a viewing angle corresponding to an acquisition region of the camera in the transverse direction, and L is a view width corresponding to the reference view in the transverse direction.

7. The lesion locating method according to claim 5, wherein at least two cameras are provided, comprising a first camera and a second camera, wherein the actual locating trajectory is calculated from corresponding reference views formed by the two cameras, the first camera and the second camera are symmetrically distributed on two sides of the sector-scanning plane of the ultrasound probe, and have a same height difference from the ultrasound probe, the first camera acquires data and forms a first reference view, and the second camera acquires data and forms a second reference view;

calculating the actual transverse displacement comprises calculating the actual transverse displacement from a position of the virtual mark point in the first reference view and a position of the virtual mark point in the second reference view, wherein a calculation formula of the actual transverse displacement satisfies:

$$y = \frac{\tan\left(\frac{L_2}{L}\theta\right) - \tan\left(\frac{L_1}{L}\theta\right)}{\tan\left(\frac{L_1}{L}\theta\right) + \tan\left(\frac{L_2}{L}\theta\right)} a$$

where y is an actual transverse displacement component, a is a center distance between the ultrasound probe and each camera, $L_1$ is a transverse distance between the virtual mark point in the first reference view and a view center; and $L_2$ is a transverse distance between the virtual mark point in the second reference view and the view center; images acquired by the first camera and the second camera each have a viewing angle $\theta$ in the transverse direction; and the first reference view and the second reference view each have a preset view width L.

8. The lesion locating method according to claim 4, wherein at least two cameras are provided, comprising a first camera and a second camera, wherein the actual locating trajectory is calculated from corresponding reference views formed by the two cameras, the first camera and the second camera are distributed on two sides of the sector-scanning plane of the ultrasound probe, at least one of the first camera or the second camera has a center line deviating from a midperpendicular plane of the sector-scanning plane of the ultrasound probe, and the first camera and the second camera have a same height difference from the ultrasound probe, the first camera acquires data and forms a first reference view, and the second camera acquires data and forms a second reference view, and calculating the actual locating trajectory comprises: calculating a virtual transverse displacement and a virtual longitudinal displacement according to positions of the virtual mark point in the first reference view and the second reference view; and calculating an actual transverse displacement and an actual longitudinal displacement according to the virtual transverse displacement, the virtual longitudinal displacement and the imaging proportional relation; wherein in calculation of the virtual transverse displacement and the virtual longitudinal displacement, a virtual projection point of the center line of the ultrasound probe is taken as an origin, a virtual sector-scanning projection line of the sector-scanning plane of the ultrasound probe is taken as a Y axis, and a virtual midperpendicular projection line of the midperpendicular plane of the sector-scanning plane of the ultrasound probe is taken as an X axis to establish a coordinate system, and according to the positions of the virtual mark point in the first reference view and the second reference view, a coordinate calculation formula set of the virtual mark point is established:

$$y_1 = (\tan\theta_1)x_1 + b_1 - a_1\tan\theta_1;$$

$$y_1 = (\tan\theta_2)x_1 + b_2 - a_2\tan\theta_2;$$

where coordinates of the virtual mark point 41 are $(x_1, y_1)$, $\theta_1$ is an angle between the virtual mark point 41 and the sector-scanning plane of the ultrasound probe (corresponding to the X axis) in the first reference view 4a, a coordinate position of the first camera 21 is $(a_1, b_1)$, a coordinate position of the second camera 22 is $(a_2, b_2)$, and $\theta_2$ is an angle between the virtual mark point 41 and the sector-scanning plane of the ultrasound probe (corresponding to the X axis) in the second reference view 4b.

9. The lesion locating method according to claim 4, wherein cameras are divided into at least two camera groups, each of which comprises one or two cameras, an actual locating trajectory to be verified is formed according to a reference view acquired and formed by a camera group, and a final actual locating trajectory is obtained according to at least two actual locating trajectories to be verified, and wherein:

at least two cameras are provided, comprising a first camera and a second camera, wherein the first camera and the second camera are symmetrically distributed on two sides of the sector-scanning plane of the ultrasound probe, and each have a center line on a midperpendicular plane of the sector-scanning plane of the ultrasound probe and a same height difference from the ultrasound probe, and while locating a lesion, a first actual locating trajectory is calculated from a corresponding reference view formed by the first camera or the second camera, a second actual locating trajectory is calculated from corresponding reference views formed by the first camera and the second camera, and a final actual locating trajectory is determined from the first actual locating trajectory and the second actual locating trajectory;

or at least two cameras are provided, comprising a first camera and a second camera, wherein the first camera and the second camera are distributed on two sides of the sector-scanning plane of the ultrasound probe, a center line of the first camera is located on the midperpendicular plane of the sector-scanning plane of the ultrasound probe, while a center line of the second camera deviates from the midperpendicular plane of the sector-scanning plane of the ultrasound probe, the first camera and the second camera have a same height difference from the ultrasound probe, and while locating a lesion, a first actual locating trajectory is calculated from a corresponding reference view formed by the first camera, a second actual locating trajectory is calculated from corresponding reference views formed by the two cameras, and a final actual locating trajectory is determined from the first actual locating trajectory and the second actual locating trajectory;

or at least three cameras are provided, comprising a first camera, a second camera and a third camera, wherein the first camera and the third camera are distributed on one side of the sector-scanning plane of the ultrasound probe, the second camera is distributed on the other side of the sector-scanning plane of the ultrasound probe, a center line of the third camera is located on the midperpendicular plane of the sector-scanning plane of the ultrasound probe, while center lines of the first camera and the second camera deviate from the midperpendicular plane of the sector-scanning plane of the ultrasound probe, the first camera, the second camera and the third camera have a same height difference from the ultrasound probe, and while locating a lesion, a first actual locating trajectory is calculated from a corresponding reference view formed by the third camera, a second actual locating trajectory is calculated from corresponding reference views formed by the first camera and the second camera, and a final actual locating trajectory is determined from the first actual locating trajectory and the second actual locating trajectory;

or at least four cameras are provided, comprising a first camera, a second camera, a third camera and a fourth camera, wherein the first camera and the second camera are symmetrically distributed on two sides of the sector-scanning plane of the ultrasound probe, and each have a center line on the midperpendicular plane of the sector-scanning plane of the ultrasound probe, while the third camera and the fourth camera are distributed on two sides of the sector-scanning plane of the ultrasound probe, and each have a center line deviating from the midperpendicular plane of the sector-scanning plane of the ultrasound probe, a first actual locating trajectory is calculated from corresponding reference views formed by the first camera and the second camera, a second actual locating trajectory is calculated from corresponding reference views formed by the third camera and the fourth camera, and a final actual locating trajectory is determined from the first actual locating trajectory and the second actual locating trajectory;

or at least four cameras are provided, comprising a first camera, a second camera, a third camera and a fourth camera, wherein the first camera and the second camera are symmetrically distributed on two sides of the sector-scanning plane of the ultrasound probe, and each have a center line on the midperpendicular plane of the sector-scanning plane of the ultrasound probe, while the third camera and the fourth camera are distributed on two sides of the sector-scanning plane of the ultrasound probe, and each have a center line deviating from the midperpendicular plane of the sector-scanning plane of the ultrasound probe, a first actual locating trajectory is calculated from corresponding reference views formed by the first camera and the second camera, a second actual locating trajectory is calculated from corresponding reference views formed by the third camera and the fourth camera, a third actual locating trajectory is calculated from a corresponding reference view formed by the first camera or the second camera, and a final actual locating trajectory is determined from the first actual locating trajectory, the second actual locating trajectory, and the third actual locating trajectory.

10. The lesion locating method according to claim 4, wherein further comprising:

merging, according to the actual positional relationship of the camera and the ultrasound probe, the center line of the ultrasound probe in the reference view as a virtual projection point, and determining the actual locating trajectory, comprising: determining, according to a positional relationship of the virtual mark point and the virtual projection point in the reference view, a movement direction corresponding to coincidence of the virtual projection point and the virtual mark point, and controlling movement of the ultrasound probe according to the movement direction until the virtual projection point and the virtual mark point coincide with each other in the reference view.

11. The lesion locating method according to claim 1, wherein a reference scale with fixed position and shape is set corresponding to the reference view, and wherein the reference scale has corresponding scale values which are converted into and displayed as size values corresponding to the actual acquisition region of the camera according to an imaging proportion.

12. A lesion locating system, for locating a lesion by locating a mark on a body surface, said system comprising:

an image acquisition assembly having an ultrasound probe, and at least one camera distributed on one side or both sides of a sector-scanning plane of the ultrasound probe and fixed in position relative to the ultrasound probe, and a center line of the camera is parallel to a center line of the ultrasound probe;

a reference image display device configured to display a reference view, wherein the reference view is formed according to data acquired in real time by the camera, the reference view has a size of a fixed value, and a virtual mark point corresponding to the mark is formed in the reference view; and a processor comprising an actual locating trajectory calculation unit configured to calculate, according to a position of the virtual mark point in the reference view and an actual positional relationship of the camera and the ultrasound probe, an actual locating trajectory that enables the center line of the ultrasound probe to coincide with the mark.

13. The lesion locating system according to claim 12, further comprising:

a pre-locating instruction input unit configured to input a pre-locating instruction, according to which the image acquisition assembly is moved to a position above the mark; and an actuating mechanism configured to drive the image acquisition assembly to move;

wherein the processor comprises a pre-locating processing unit configured to control the actuating mechanism to move according to the pre-locating instruction, judge, after an action corresponding to the pre-locating instruction is completed by the actuating mechanism, whether a current view acquired and formed by the camera contains a virtual mark point corresponding to the mark, and take, if the current view contains the virtual mark point corresponding to the mark, the current view as the reference view.

14. The lesion locating system according to claim 13, wherein the actual locating trajectory calculation unit has a motion boundary condition calculation subunit for calculating a motion boundary condition, and the motion boundary condition calculation subunit is configured to limit, according to the pre-locating height, a motion boundary condition of the image acquisition assembly so that the ultrasound probe is movable within a preset plane, wherein the preset plane is a plane perpendicular to the center line of the ultrasound probe and corresponding to the pre-locating height.

15. The lesion locating system according to claim 13, wherein the processor further comprises an imaging unit configured to: establish an imaging proportional relation between the current view and an actual acquisition region of the camera, and form the reference view according to the imaging proportional relation;

set a preset value of the pre-locating height, and input a pre-locating instruction so that the pre-locating height is equal to the preset value and the proportional relation is a fixed value;

or establish a calculation model of the imaging proportional relation by taking the preset value of the pre-locating height as a variable, and calculate an actual imaging proportional relation after obtaining a value of the pre-locating height;

or set an installation position of the camera so that part of a side edge contour of the ultrasound probe always exists in the current view acquired by the camera, and calculate, when establishing the imaging proportional relation, the imaging proportional relation from an actual distance from the center line of the camera to the side edge contour and a reference distance in the reference view.

16. The lesion locating system according to claim 15, wherein the center line of the camera is located on a midperpendicular plane of the sector-scanning plane of the ultrasound probe, so the imaging unit is configured to: form the reference view so that the center line of the camera is located at a center of the reference view, wherein the reference view takes a projection of the midperpendicular plane of the ultrasonic sector-scanning plane as a transverse axis and a direction perpendicular to the transverse axis as a longitudinal direction; and the actual locating trajectory calculation unit comprises an actual transverse displacement calculation subunit and an actual longitudinal displacement calculation subunit, wherein the actual longitudinal displacement calculation subunit is configured to: move, according to a position of the virtual mark point in the reference view, the virtual mark point to a virtual longitudinal displacement desired to coincide with the transverse axis, and calculate the actual longitudinal displacement according to the virtual longitudinal displacement and the imaging proportional relation.

17. The lesion locating system according to claim 16, wherein one camera is provided, and the actual transverse displacement calculation subunit is configured to: calculate a virtual transverse displacement of the virtual mark point according to the position of the virtual mark point in the reference view, and calculate the actual transverse displacement according to the virtual transverse displacement and the imaging proportional relation, wherein a calculation formula of the virtual transverse displacement satisfies:

$$L_0 = \frac{\arctan\dfrac{h_1 + h_2}{a} - \dfrac{\pi - \theta}{2}}{\theta} \times L$$

where $L_0$ is a virtual transverse displacement component, a is a center distance between the ultrasound probe and the camera, $h_1$ is a height distance between the ultrasound probe and the camera, $h_2$ is the pre-locating height, $\theta$ is a viewing angle corresponding to an acquisition region of the camera in the transverse direction, and L is a view width corresponding to the reference view in the transverse direction.

18. The lesion locating system according to claim 17, wherein two cameras are provided, comprising a first camera and a second camera, wherein the first camera and the second camera are symmetrically distributed on two sides of the sector-scanning plane of the ultrasound probe, and have a same height difference from the ultrasound probe;

the imaging unit is configured to: form a first reference view from data acquired by the first camera, and form a second reference view from data acquired by the second camera; and the actual transverse displacement calculation subunit is configured to: calculate the actual transverse displacement from a position of the virtual mark point in the first reference view and a position of the virtual mark point in the second reference view, wherein a calculation formula of the actual transverse displacement satisfies:

$$y = \frac{\tan\left(\dfrac{L_2}{L}\theta\right) - \tan\left(\dfrac{L_1}{L}\theta\right)}{\tan\left(\dfrac{L_1}{L}\theta\right) + \tan\left(\dfrac{L_2}{L}\theta\right)}a$$

where y is an actual transverse displacement component, a is a center distance between the ultrasound probe and each camera, $L_1$ is a transverse distance between the virtual mark point in the first reference view and a view center; and $L_2$ is a transverse distance between the virtual mark point in the second reference view and the view center; images acquired by the first camera and the second camera each have a viewing angle $\theta$ in the transverse direction; and the first reference view and the second reference view each have a preset view width L.

19. The lesion locating system according to claim 15, wherein two cameras are provided, comprising a first camera and a second camera, wherein the first camera and the second camera are distributed on two sides of the sector-scanning plane of the ultrasound probe, at least one of the first camera or the second camera has a center line deviating from a midperpendicular plane of the sector-scanning plane of the ultrasound probe, and the first camera and the second camera have a same height difference from the ultrasound probe;

the imaging unit is configured to: form a first reference view from data acquired by the first camera, and form a second reference view from data acquired by the second camera; and the actual locating trajectory calculation unit is configured to: calculate a virtual transverse displacement and a virtual longitudinal displacement according to positions of the virtual mark point in the first reference view and the second reference view; and calculate an actual transverse displacement and an actual longitudinal displacement according to the virtual transverse displacement, the virtual longitudinal displacement and the imaging proportional relation; wherein in calculation of the virtual transverse displacement and the virtual longitudinal displacement, a virtual projection point of the center line of the ultrasound probe is taken as an origin, a virtual sector-scanning projection line of the sector-scanning plane of the ultrasound probe is taken as a Y axis, and a virtual midperpendicular projection line of the midperpendicular plane of the sector-scanning plane of the ultrasound probe is taken as an X axis to establish a coordinate system, and according to the positions of the virtual mark point in the first reference view and the second reference view, a coordinate calculation formula set of the virtual mark point is established:

$$y_1 = (\tan \theta_1)x_1 + b_1 - a_1 \tan \theta_1;$$

$$y_1 = (\tan \theta_2)x_1 + b_2 - a_2 \tan \theta_2;$$

where coordinates of the virtual mark point are $(x_1, y_1)$, in the first reference view, $\theta_1$ is a viewing angle of an acquisition region of the first camera in a width direction corresponding to the X axis, a coordinate position of the first camera is $(a_1, b_1)$, a coordinate position of the second camera is $(a_2, b_2)$, and $\theta_2$ is a viewing angle of an acquisition region of the second camera in the width direction corresponding to the X axis.

20. The lesion locating system according to claim 12, wherein a reference scale is provided in the reference view or on a display device of the reference view, the reference scale has corresponding scale values which are converted into and displayed as size values corresponding to the actual acquisition region of the camera according to an imaging proportion.

* * * * *